United States Patent
Arimitsu

(10) Patent No.: US 11,873,354 B2
(45) Date of Patent: Jan. 16, 2024

(54) PHOTOBASE GENERATOR, COMPOUND, PHOTOREACTIVE COMPOSITION, AND REACTION PRODUCT

(71) Applicant: Tokyo University of Science Foundation, Tokyo (JP)

(72) Inventor: Koji Arimitsu, Tokyo (JP)

(73) Assignee: Tokyo University of Science Foundation, Tokyo (JP)

( * ) Notice: Subject to any disclaimer, the term of this patent is extended or adjusted under 35 U.S.C. 154(b) by 182 days.

(21) Appl. No.: 17/641,574

(22) PCT Filed: Sep. 10, 2020

(86) PCT No.: PCT/JP2020/034262
§ 371 (c)(1),
(2) Date: Mar. 9, 2022

(87) PCT Pub. No.: WO2021/049563
PCT Pub. Date: Mar. 18, 2021

(65) Prior Publication Data
US 2022/0298268 A1 Sep. 22, 2022

(30) Foreign Application Priority Data

Sep. 10, 2019 (JP) .................................. 2019-164946

(51) Int. Cl.
| | |
|---|---|
| *C08F 2/50* | (2006.01) |
| *C08F 122/10* | (2006.01) |
| *C07C 59/11* | (2006.01) |
| *C07C 69/732* | (2006.01) |
| *C07C 279/04* | (2006.01) |
| *C07C 279/22* | (2006.01) |
| *C07D 233/06* | (2006.01) |
| *C07D 295/185* | (2006.01) |
| *C07D 311/86* | (2006.01) |
| *C08G 59/50* | (2006.01) |

(52) U.S. Cl.
CPC .............. *C08F 2/50* (2013.01); *C07C 59/11* (2013.01); *C07C 69/732* (2013.01); *C07C 279/04* (2013.01); *C07C 279/22* (2013.01); *C07D 233/06* (2013.01); *C07D 295/185* (2013.01); *C07D 311/86* (2013.01); *C08F 122/1006* (2020.02); *C08G 59/5046* (2013.01)

(58) Field of Classification Search
None
See application file for complete search history.

(56) References Cited

U.S. PATENT DOCUMENTS

| | | | | |
|---|---|---|---|---|
| 8,288,591 B2 * | 10/2012 | Dershem | ............ | C08G 59/4007 525/523 |
| 8,476,444 B2 * | 7/2013 | Katayama | .............. | C08G 73/10 546/226 |
| 8,778,596 B2 * | 7/2014 | Katayama | ............... | C08L 79/04 430/913 |
| 2013/0012620 A1 * | 1/2013 | Dershem | ................ | C09J 163/00 548/338.1 |

FOREIGN PATENT DOCUMENTS

| | | |
|---|---|---|
| IN | 177137 B | 11/1996 |
| JP | 2015194720 A | * 11/2015 |
| JP | 2019189539 A | * 10/2019 |

OTHER PUBLICATIONS

Arimitsu et al. "Application to Photoreactive Materials of Photochemical Generation of Superbases with High Efficiency Based on Photodecarboxylation Reactions" Chem.Mater.2013, 25, 4461-4463.

Cameron et al. "Photogeneration of Organic Bases from o-Nitrobenzyl-Derived Carbamates" J.Am.Chem.Soc.1991, 113, 4303.

* cited by examiner

*Primary Examiner* — Sanza L. McClendon
(74) *Attorney, Agent, or Firm* — Banner & Witcoff, Ltd.

(57) ABSTRACT

A photobase generator includes a compound including a first skeleton represented by the following formula (a), and a second skeleton including a nitrogen atom bonding to a bonding position of the first skeleton to form an amide group, wherein the compound generates a base, in which a hydrogen atom is bonding with the nitrogen atom of the second skeleton, by light irradiation, and the pKa of a conjugate acid of the base in water is 12 or more. In formula (a), G is a divalent aromatic group, and * represents the bonding position with the nitrogen atom.

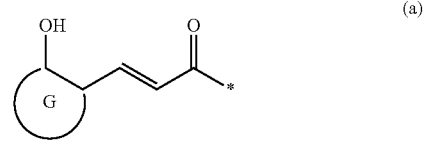

(a)

9 Claims, 18 Drawing Sheets

PHOTOBASE GENERATOR, COMPOUND, PHOTOREACTIVE COMPOSITION, AND REACTION PRODUCT

CROSS-REFERENCE TO RELATED APPLICATIONS

This application is a National Stage Application under 35 U.S.C. 371 of co-pending PCT application number PCT/JP2020/034262 designating the United States and filed Sep. 10, 2020, which claims the benefit of JP application number 2019-164946 and filed Sep. 10, 2019, each of which are hereby incorporated by reference in their entireties.

TECHNICAL FIELD

The present invention relates to a photobase generator, a compound, a photoreactive composition, and a reaction product.

BACKGROUND ART

Photopolymerizable materials to be polymerized when irradiated with light are widely practically used, and hold predominant positions in the fields of, for example, electronic materials or printing materials, because polymerization reactions thereof can be precisely controlled by relatively simple operations.

Photopolymerizable materials which have been heretofore actively studied are, for example, a radical polymerization resin composition including a photoinitiator that generates radical species by exposure, and a radical-polymerizable monomer or oligomer, and an acid catalyst-based resin composition including a photoacid generator that generates acid by exposure, and a monomer or oligomer to be polymerized by the action of an acid.

Base catalyst-based photopolymerizable materials are also known as photopolymerizable materials, such a base catalyst-based photopolymerizable material including a photobase generator that generates base by exposure, and a monomer or oligomer to be polymerized by the action of a base. A photobase generator known is, for example, an ionic photobase generator corresponding to a salt of a strong base such as guanidine and a carboxylic acid (see, for example, Non-Patent Literature 1). In such an ionic photobase generator, along with progression of a decarboxylation reaction in a carboxy group by exposure, a base is generated by elimination of the strong base forming the salt together with the carboxy group.

However, such an ionic photobase generator has a problem of being low in stability during storage and low in solubility, although high in reactivity. A resin composition using such an ionic photobase generator also has the problem of being low in stability.

On the contrary, non-ionic photobase generators have also been studied. A non-ionic photobase generator known is, for example, a non-ionic photobase generator that is a carbamate having a nitrobenzyl skeleton, in which a base is generated by not only progression of a decarboxylation reaction by exposure, but also elimination of a primary amine or secondary amine (see, for example, Non-Patent Literature 2). Such a non-ionic photobase generator allows the above problems about ionic photobase generators to be solved.

CITATION LIST

Non-Patent Literature

[Non-Patent Literature 1] K. Arimitsu, R. Endo, Chem. Mater. 2013, 25, 4461-4463.

[Non-Patent Literature 2] J. F. Cameron, J. M. J. Frechet, J. Am. Chem. Soc. 1991, 113, 4303.

SUMMARY OF INVENTION

Technical Problem

However, because a non-ionic photobase generator disclosed in the Non-Patent Literature 2 generate a weak base, a resin composition using it still had room for improvement in terms of improving reactivity when irradiated with light. Further, in the non-ionic photobase generator disclosed in the Non-Patent Literature 2, there is a problem that a decarboxylation reaction occurs with the generation of the base due to exposure.

An object of the invention is to provide a photobase generator and a compound excellent in the reactivity when irradiated with light and capable of preparing a photoreactive composition in which a decarboxylation reaction does not occur when irradiated with light, a photoreactive composition, excellent in the reactivity when irradiated with light, in which a decarboxylation reaction does not occur when irradiated with light, and a reaction product obtained by reacting the photoreactive composition.

Solution to Problem

Specific means for solving the above problem are shown below.

<1> A photobase generator, comprising a compound including a first skeleton represented by the following formula (a), and a second skeleton including a nitrogen atom bonding to a bonding position of the first skeleton to form an amide group, wherein the compound generates a base, in which a hydrogen atom is bonding with the nitrogen atom of the second skeleton, by light irradiation, and the pKa of a conjugate acid of the base in water is 12 or more.

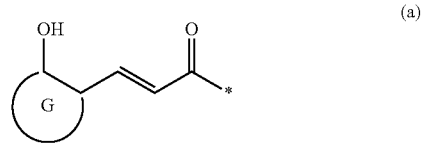

(a)

(In formula (a), G is a divalent aromatic group, and * represents the bonding position with the nitrogen atom.)

<2> The photobase generator according to <1>, wherein the second skeleton is a structure represented by the following formula (1)-12, (1)-13, or (1)-14.

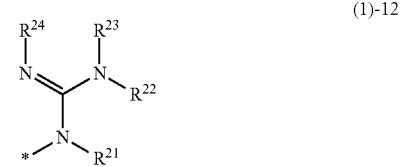

(1)-12

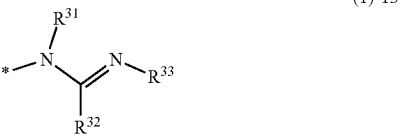

(1)-13

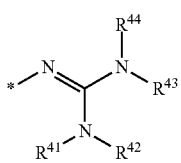
(1)-14

(In formula (1)-12 to formula (1)-14, each of $R^{22}$, $R^{23}$, $R^{24}$, $R^{32}$, $R^{33}$, $R^{41}$, $R^{42}$, $R^{43}$, and $R^{44}$ independently represents a hydrogen atom or a hydrocarbon group that may have a substituent; each of $R^{21}$ and $R^{31}$ independently represents a hydrocarbon group that may have a substituent; * represents a bonding position that forms a single bond by combining with * in formula (a); two or more of $R^{21}$ to $R^{24}$ are optionally bonding to each other to form a ring structure; two or more of $R^{31}$ to $R^{33}$ are optionally bonding to each other to form a ring structure; and two or more of $R^{41}$ to $R^{44}$ are optionally bonding to each other to form a ring structure.)

<3> A photobase generator, comprising a compound including a first skeleton represented by the following formula (a), and a second skeleton that includes a nitrogen atom bonding to a bonding position of the first skeleton to form an amide group and that is represented by the following formula (1)-12, (1)-13, or (1)-14, wherein the compound generates a base, in which a hydrogen atom is bonding with the nitrogen atom of the second skeleton, by light irradiation.

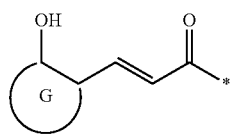
(a)

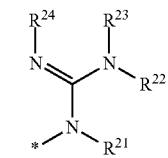
(1)-12

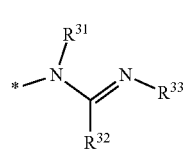
(1)-13

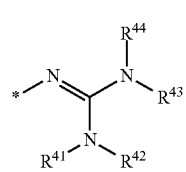
(1)-14

(In formula (a), G is a divalent aromatic group, and * represents the bonding position with the nitrogen atom; and in formula (1)-12 to formula (1)-14, each of $R^{22}$, $R^{23}$, $R^{24}$, $R^{32}$, $R^{33}$, $R^{41}$, $R^{42}$, $R^{43}$, and $R^{44}$ independently represents a hydrogen atom or a hydrocarbon group that may have a substituent; each of $R^{21}$ and $R^{31}$ independently represents a hydrocarbon group that may have a substituent; * represents a bonding position that forms a single bond by combining with * in formula (a); two or more of $R^{21}$ to $R^{24}$ are optionally bonding to each other to form a ring structure; two or more of $R^{31}$ to $R^{33}$ are optionally bonding to each other to form a ring structure; two or more of $R^{41}$ to $R^{44}$ are optionally bonding to each other to form a ring structure; and in a case in which a structure represented by in formula (1)-13 has a ring structure formed by bonding $R^{31}$ and $R^{33}$ to each other, the ring structure does not exhibit aromaticity.)

<4> A compound, comprising a first skeleton represented by the following formula (a), and a second skeleton including a nitrogen atom bonding to a bonding position of the first skeleton to form an amide group, wherein the compound generates a base, in which a hydrogen atom is bonding with the nitrogen atom of the second skeleton, by light irradiation, and the pKa of a conjugate acid of the base in water is 12 or more.

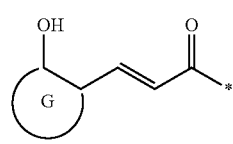
(a)

(In formula (a), G is a divalent aromatic group; and * represents the bonding position with the nitrogen atom.)

<5> The compound according to 4, wherein the second skeleton is a structure represented by the following formula (1)-12, (1)-13, or (1)-14.

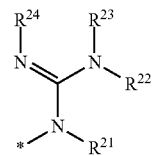
(1)-12

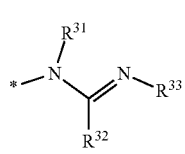
(1)-13

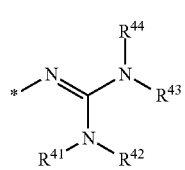
(1)-14

(In formula (1)-12 to formula (1)-14, each of $R^{22}$, $R^{23}$, $R^{24}$, $R^{32}$, $R^{33}$, $R^{41}$, $R^{42}$, $R^{43}$, land $R^{44}$ independently represents a hydrogen atom or a hydrocarbon group that may have a substituent; each of $R^{21}$ and $R^{31}$ independently represents a hydrocarbon group that may have a substituent; * represents a bonding position that forms a single bond by combining with * in the formula (a); two or more of $R^{21}$ to $R^{24}$ are optionally bonding to each other to form a ring structure; two or more of $R^{31}$ to $R^{33}$ are optionally bonding to each other to form a ring structure; and two or more of $R^{41}$ to $R^{44}$ are optionally bonding to each other to form a ring structure.)

<6> A compound, comprising a first skeleton represented by the following formula (a), and a second skeleton that includes a nitrogen atom bonding to a bonding position of the first skeleton to form an amide group and that is represented by the following formula (1)-12, (1)-13, or (1)-14, wherein the compound generates a base, in which a hydrogen atom is bonding with the nitrogen atom of the second skeleton, by light irradiation.

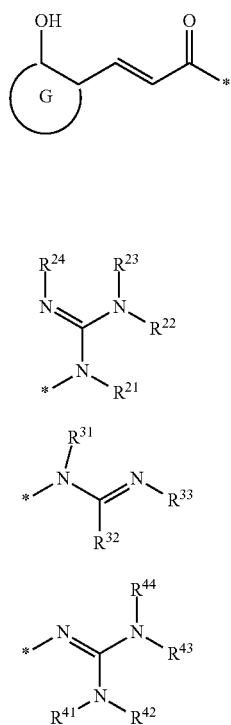

(In formula (a), G is a divalent aromatic group, and * represents the bonding position with the nitrogen atom; and in formula (1)-12 to formula (1)-14, each of $R^{22}$, $R^{23}$, $R^{24}$, $R^{32}$, $R^{33}$, $R^{41}$, $R^{42}$, $R^{43}$, and $R^{44}$ independently represents a hydrogen atom or a hydrocarbon group that may have a substituent; each of $R^{21}$ and $R^{31}$ independently represents a hydrocarbon group that may have a substituent; * represents a bonding position that forms a single bond by combining with * in the formula (a); two or more of $R^{21}$ to $R^{24}$ are optionally bonding to each other to form a ring structure; two or more of $R^{31}$ to $R^{33}$ are optionally bonding to each other to form a ring structure; two or more of $R^{41}$ to $R^{44}$ are optionally bonding to each other to form a ring structure; and in a case in which a structure represented by in formula (1)-13 has a ring structure formed by bonding $R^{31}$ and $R^{33}$ to each other, the ring structure does not exhibit aromaticity.)

<7> A photoreactive composition, comprising: the photobase generator according to any one of <1> to <3>; and a base-reactive compound, wherein the base-reactive compound includes a functional group that is converted, by the action of a base, into a group exhibiting reactivity, or includes a group that reacts in response to the action of a base.

<8> A reaction product obtained by reacting the photoreactive composition according to <7>.

Advantageous Effects of Invention

The invention can provide a photobase generator and a compound excellent in the reactivity when irradiated with light and capable of preparing a photoreactive composition in which a decarboxylation reaction does not occur when irradiated with light, a photoreactive composition, excellent in the reactivity when irradiated with light, in which a decarboxylation reaction does not occur when irradiated with light, and a reaction product obtained by reacting the photoreactive composition.

DESCRIPTION OF EMBODIMENTS

Figure 1:
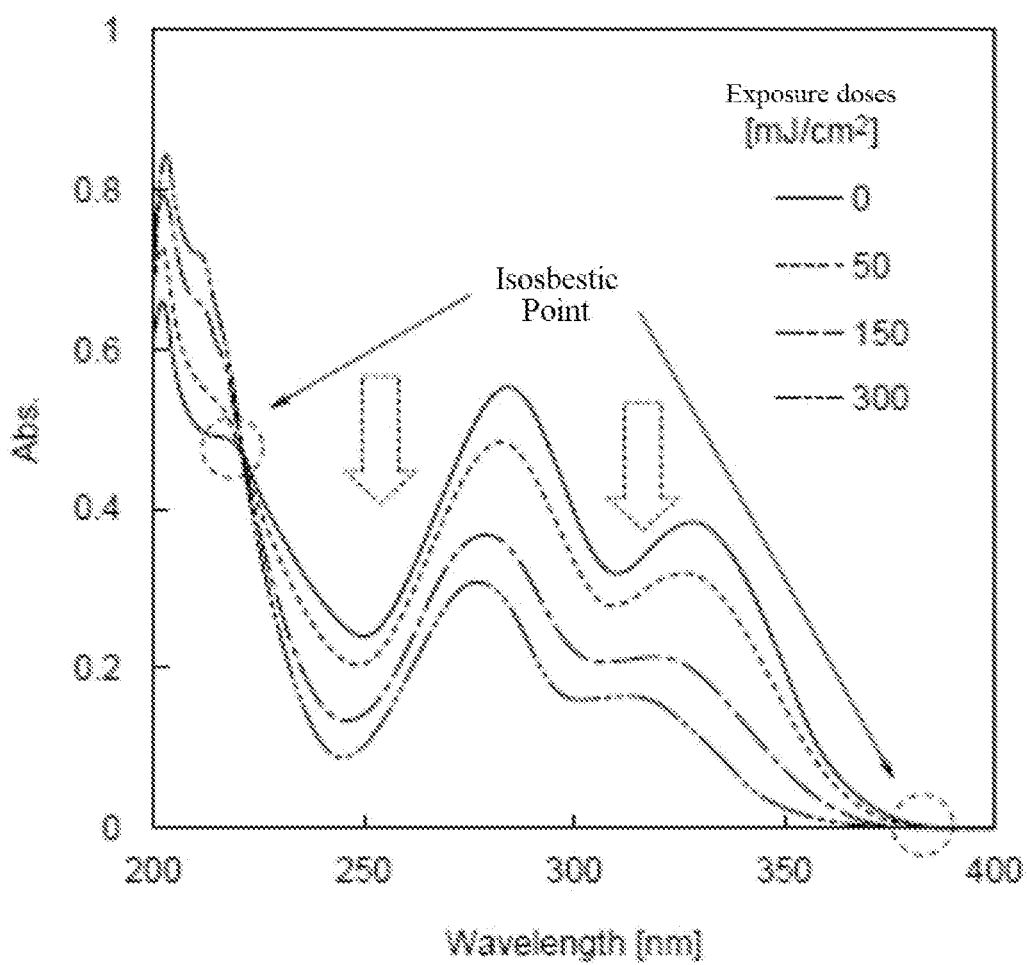
FIG. 1 is data that illustrates the measurement result of the absorbance of a compound (1)-1 in Test Example 1.

A numerical value range herein represented by "(from) . . . to . . . " means that numerical values described before and after "to" are encompassed as the lower limit and the upper limit, respectively.

Photobase Generator

A photobase generator in the disclosure includes a compound including a first skeleton represented by the following formula (a), and a second skeleton including a nitrogen atom bonding to a bonding position of the first skeleton to form an amide group, the compound generates a base, in which a hydrogen atom is bonding with the nitrogen atom of the second skeleton, by light irradiation, and the pKa of a conjugate acid of the base in water is 12 or more.

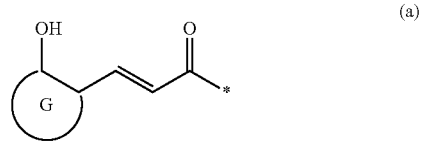

(a)

In formula (a), G is a divalent aromatic group, and * represents the bonding position with the nitrogen atom.

For example, the photobase generator in the disclosure is used for preparation of a photoreactive composition capable of manufacturing a reaction product by light irradiation. More specifically, the base is generated from the photobase generator by irradiating the photoreactive composition including the photobase generator with light. The functional group, which is included in the base-reactive compound of the photoreactive composition, is converted by the action of the base to exhibit reactivity, or the functional group, which is included in the base-reactive compound, reacts by the action of the base. Thus, the aforementioned photoreactive composition is irradiated with light to generate a base, thereby allowing the base-reactive compound included in the photoreactive composition to be reacted, and the reaction product is obtained.

The photobase generator includes the compound (in the disclosure, also referred to as "compound (1)") including the first skeleton represented by the formula (a), and the second skeleton (X in the following formula (i)) including a nitrogen atom bonding to a bonding position of the first skeleton to form the amide group. The compound (1) generates the base by light irradiation. Further, the compound (1) is converted into a cis form by light irradiation, and then the oxygen atom of the hydroxyl group in the formula (a) and the carbonyl carbon in the formula (a) is bonding and the nitrogen atom in the second skeleton bonding to the carbonyl carbon dissociates and bonds with the hydrogen atom. Thereby, the compound represented by the following formula (1') and the amine compound represented by HX are generated. The generated amine compound is the base and the pKa of the conjugate acid of the base in water is 12 or more.

Further, the compound (1) is a non-ionic photobase generator, and unlike the conventional ionic photobase generator, it has high stability during preservation and high solubility, and the photoreactive composition using this has high stability. In the photoreactive composition using the photobase generator including the compound (1), the reactivity of the base-reactive compound when irradiated with light is good because the pKa of the conjugated acid of the generated base is 12 or more in water.

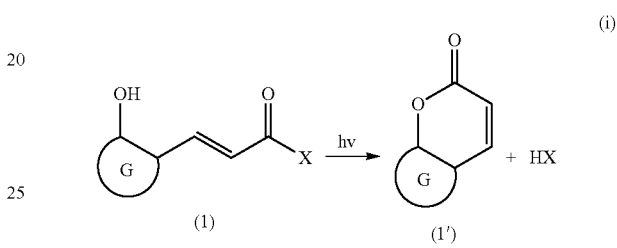

In the compound (1), the pKa of the conjugate acid of the base in water is preferably 14 or more, and more preferably 16 or more, from the point of the reactivity when irradiated with light.

As a conventionally known non-ionic photobase generator, for example, a carbamate having a nitrobenzyl skeleton shown below is known. When such a carbamate having the nitrobenzyl skeleton is irradiated with light, a decarboxylation reaction proceeds as shown in the following formula (ii), and a base (primary amine in the following reaction formula) is generated.

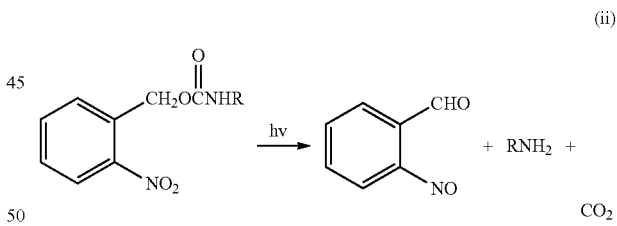

On the other hand, in the compound (1) included in the photobase generator according to the present invention, as shown in the aforementioned formula (i), a decarboxylation reaction does not proceed by light irradiation. Thus, it is possible to prevent the generation of bubbles due to the generation of carbon dioxide, and the decrease in strength when the reaction product is a cured product.

In Formula (a), G is a divalent aromatic group, and a hydroxyl group and —CH═CH—C(═O)—* are bonding.

The respective bonding positions of a hydroxyl group and —CH═CH—C(═O)—* to G are in an ortho-position. In other words, an atom to which a hydroxyl group is bonding and an atom to which —CH═CH—C(═O)—* is bonding, among atoms included in a ring skeleton of G, are adjacent (directly bonding) to each other in the ring skeleton of G.

The aromatic group in G may be any of a divalent aromatic hydrocarbon group or a divalent aromatic heterocyclic group, or may be a divalent group (in the disclosure, such a group is regarded as an aromatic heterocyclic group) obtained by ring fusion of an aromatic hydrocarbon group and an aromatic heterocyclic group.

The aromatic hydrocarbon group and the aromatic heterocyclic group may have a substituent.

The "aromatic hydrocarbon group having a substituent" means that one or more hydrogen atoms included in the aromatic hydrocarbon group is substituted with any group (substituent) other than a hydrogen atom.

The "aromatic heterocyclic group having a substituent" means that one or more hydrogen atoms included in the aromatic heterocyclic group is substituted with any group (substituent) other than a hydrogen atom.

The aromatic group in G may be either monocyclic or polycyclic, and the number of atoms (number of ring members) included in the ring skeleton is not particularly limited, and is preferably from 3 to 20.

Examples of the aromatic hydrocarbon group as the aromatic group in G include a 1,2-phenylene group, a naphthalene-1,2-diyl group, a naphthalene-2,3-diyl group, a toluene-2,3-diyl group, a toluene-3,4-diyl group, an o-xylene-3,4-diyl group, an o-xylene-4,5-diyl group, an m-xylene-4,5-diyl group, a p-xylene-2,3-diyl group, an anthracene-1,2-diyl group, and an anthracene-2,3-diyl group. One or more hydrogen atoms in the aromatic hydrocarbon group may be each substituted with a substituent, for example, the aromatic hydrocarbon group or alkyl group exemplified. The aromatic hydrocarbon group having such a substituent preferably has from 6 to 20 carbon atoms also including carbon atom(s) of the substituent.

The alkyl group (hereinafter, sometimes referred to as "substituent alkyl group") with which one or more hydrogen atoms of the aromatic hydrocarbon group exemplified are/is substituted may be any of a linear, branched, or cyclic alkyl group, and may be any of a monocyclic or polycyclic alkyl group in a case in which the alkyl group is a cyclic alkyl group. The substituent alkyl group preferably has from 1 to 10 carbon atoms.

The linear or branched substituent alkyl group preferably has from 1 to 10 carbon atoms, and examples include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a 1-methylbutyl group, a n-hexyl group, a 2-methylpentyl group, a 3-methylpentyl group, a 2,2-dimethylbutyl group, a 2,3-dimethylbutyl group, a n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, a n-octyl group, an isooctyl group, a 2-ethylhexyl group, a nonyl group, and a decyl group.

The cyclic substituent alkyl group preferably has from 3 to 10 carbon atoms, and examples thereof include a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, a 1-adamantyl group, a 2-adamantyl group, and a tricyclodecyl group, and further include such a cyclic alkyl group in which one or more hydrogen atoms are/is substituted with a linear, branched, or cyclic alkyl group. Examples of the linear, branched, or cyclic alkyl group with which hydrogen atom(s) are/is substituted include the same as in the substituent alkyl group.

Examples of the aromatic heterocyclic group as the aromatic group in G include a group obtained by removing two hydrogen atoms each bonding to a carbon atom or a hetero atom included in the ring skeleton, from such each aromatic heterocyclic compound.

Preferable examples of the aromatic heterocyclic compound include a compound having one or more sulfur atoms as atom(s) included in the aromatic heterocyclic skeleton (sulfur-containing aromatic heterocyclic compound), a compound having one or more nitrogen atoms as atom(s) included in the aromatic heterocyclic skeleton (nitrogen-containing aromatic heterocyclic compound), a compound having one or more oxygen atoms as atom(s) included in the aromatic heterocyclic skeleton (oxygen-containing aromatic heterocyclic compound), and a compound having two hetero atoms different from each other, selected from the group consisting of a sulfur atom, a nitrogen atom, and an oxygen atom, as atoms included in the aromatic heterocyclic skeleton.

Examples of the sulfur-containing aromatic heterocyclic compound include thiophene and benzothiophene.

Examples of the nitrogen-containing aromatic heterocyclic compound include pyrrole, imidazole, pyrazole, pyridine, pyrazine, pyrimidine, pyridazine, triazine, indole, isoindole, benzimidazole, purine, indazole, quinoline, isoquinoline, quinoxaline, quinazoline, and cinnoline.

Examples of the oxygen-containing aromatic heterocyclic compound include furan, benzofuran (1-benzofuran), and isobenzofuran (2-benzofuran).

Examples of the compound having two hetero atoms different from each other, included in the aromatic heterocyclic skeleton, include oxazole, isoxazole, thiazole, benzoxazole, benzisoxazole, and benzothiazole.

As atoms included in the ring skeleton of the aromatic heterocyclic group, the atom to which a hydroxyl group is bonding and the atom to which —CH=CH—C(=O)—* is bonding, among atoms included in the ring skeleton of the aromatic heterocyclic group, may be each a carbon atom or a hetero atom, and are preferably each a carbon atom.

The number of hetero atom(s) included in the ring skeleton in the aromatic heterocyclic group is preferably from 1 to 3, and more preferably 1 or 2.

In a case in which the number of hetero atom(s) included in the ring skeleton in the aromatic heterocyclic group is two or more, such hetero atoms may be all the same, may be all different, or may be only partially the same.

Examples of the substituent in the aromatic hydrocarbon group or aromatic heterocyclic group in G include the substituent alkyl group, an alkoxy group, an aryloxy group, a dialkylamino group, a diarylamino group, an alkylarylamino group, an alkylcarbonyl group, an arylcarbonyl group, an alkyloxycarbonyl group, an aryloxycarbonyl group, an alkylcarbonyloxy group, an arylcarbonyloxy group, an alkylthio group, an arylthio group, a cyano group (—CN), a halogen atom, a nitro group, a haloalkyl group (halogenated alkyl group), a hydroxyl group (—OH), a mercapto group (—SH), an amino group the aromatic hydrocarbon group, and the aromatic heterocyclic group.

The number of such sub stituent(s) in the aromatic hydrocarbon group or aromatic heterocyclic group in G may be only one, or two or more, and all hydrogen atoms may be each substituted with any of the substituent. The number of such substituent(s) is, for example, preferably from 1 to 4, more preferably from 1 to 3, and still more preferably 1 or 2, depending on the number of hydrogen atoms that can be substituted.

In a case in which the number of such substituents in the aromatic hydrocarbon group or aromatic heterocyclic group is two or more, such substituents may be all the same, may be all different, or may be only partially the same.

Examples of the alkoxy group as the substituent include a monovalent group obtained by bonding the substituent alkyl group to an oxygen atom, for example, a methoxy group, an ethoxy group, a n-propoxy group, an isopropoxy group, or a cyclopropoxy group.

The aryl group bonding to an oxygen atom in the aryloxy group as the substituent may be any of a monocyclic or polycyclic aryl group, and preferably has from 6 to 10 carbon atoms. Examples of such an aryl group include a phenyl group, a 1-naphthyl group, a 2-naphthyl group, an o-tolyl group, a m-tolyl group, a p-tolyl group, and a xylyl group (dimethylphenyl group), and further include such an aryl group in which one or more hydrogen atoms are/is substituted with, for example, such an aryl group or the substituent alkyl group. The aryl group having such a substituent preferably has from 6 to 10 carbon atoms also including carbon atom(s) of the substituent.

Examples of the dialkylamino group as the substituent include a monovalent group obtained by substituting each of two hydrogen atoms in an amino group (—NH$_2$) with the substituent alkyl group, such as a dimethylamino group or a methylethylamino group. Such two alkyl groups bonding to a nitrogen atom in the dialkylamino group may be the same as or different from each other.

Examples of the diarylamino group as the substituent include a monovalent group obtained by substituting each of two hydrogen atoms in an amino group with the aryl group, such as a diphenylamino group or a phenyl-1-naphthylamino group. Such aryl groups bonding to a nitrogen atom in the diarylamino group may be the same as or different from each other.

Examples of the alkylarylamino group as the substituent include a monovalent group obtained by substituting one hydrogen atom of two hydrogen atoms in an amino group with the substituent alkyl group, and substituting another hydrogen atom thereof with the aryl group, such as a methylphenylamino group.

Examples of the alkylcarbonyl group as the substituent include a monovalent group obtained by bonding the substituent alkyl group to a carbonyl group (—C(=O)—), for example, a methylcarbonyl group (acetyl group).

Examples of the arylcarbonyl group as the substituent include a monovalent group obtained by bonding the aryl group to a carbonyl group, for example, a phenylcarbonyl group (benzoyl group).

Examples of the alkyloxycarbonyl group as the substituent include a monovalent group obtained by bonding the alkoxy group to a carbonyl group, for example, a methyloxycarbonyl group (methoxycarbonyl group).

Examples of the aryloxycarbonyl group as the substituent include a monovalent group obtained by bonding the aryloxy group to a carbonyl group, for example, a phenyloxycarbonyl group (phenoxycarbonyl group).

Examples of the alkylcarbonyloxy group as the substituent include a monovalent group obtained by bonding the substituent alkyl group to a carbon atom of a carbonyloxy group (—C(=O)—O—), for example, a methylcarbonyloxy group.

Examples of the arylcarbonyloxy group as the substituent include a monovalent group obtained by bonding the aryl group to a carbon atom of a carbonyloxy group, for example, a phenylcarbonyloxy group.

Examples of the alkylthio group as the substituent include a monovalent group obtained by bonding the substituent alkyl group to a sulfur atom, for example, a methylthio group, an ethylthio group, a n-propylthio group, an isopropylthio group, or a cyclopropylthio group.

Examples of the arylthio group as the substituent include a monovalent group obtained by bonding the aryl group to a sulfur atom, for example, a phenylthio group, a 1-naphthylthio group, or a 2-naphthylthio group.

Examples of the halogen atom as the substituent include a fluorine atom (—F), a chlorine atom (—Cl), a bromine atom (—Br), and an iodine atom (—I).

Examples of the haloalkyl group as the substituent include a group obtained by substituting one or more hydrogen atoms of the substituent alkyl group with halogen atom(s).

Examples of each halogen atom in the haloalkyl group include those described above, exemplified as halogen atoms serving as substituents.

The number of halogen atom(s) in the haloalkyl group is not particularly limited, and may be one, or two or more. In a case in which the number of halogen atom(s) in the haloalkyl group is two or more, such a plurality of halogen atoms may be all the same, may be all different, or may be only partially the same. The haloalkyl group may be a perhaloalkyl group in which all hydrogen atoms in the alkyl group are each substituted with a halogen atom.

The haloalkyl group is not particularly limited, and examples thereof include a chloromethyl group, a dichloromethyl group, a trichloromethyl group, and a trifluoromethyl group.

In a case in which the substituent in the aromatic hydrocarbon group or aromatic heterocyclic group in G is, for example, an electron-donating group such as an alkoxy group, an aryloxy group, a dialkylamino group, a diarylamino group, an alkylarylamino group, an alkylthio group, or an arylthio group, in the compound (1), wavelength of light necessary for generation of the base by light irradiation becomes longer (make wavelength longer). In other words, the substituent as such an electron-donating group has the advantage of enabling wavelength of light necessary for generation of the base to become longer in the compound (1).

The position of the substituent in the aromatic hydrocarbon group or aromatic heterocyclic group is not particularly limited.

G is preferably an aromatic hydrocarbon group optionally having a substituent, such a substituent is more preferably an aromatic hydrocarbon group optionally having one or more in total of one or more kinds selected from the group consisting of an alkoxy group, an aryloxy group, a dialkylamino group, a diarylamino group, an alkylarylamino group, an alkylthio group, and an arylthio group, and examples of such G include a group represented by the following Formula (a)-1.

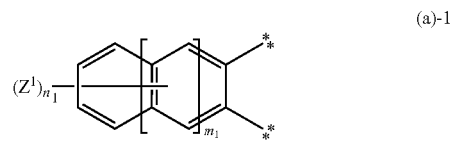

(a)-1

In Formula (a)-1, $m_1$ is an integer of 0 to 2; $n_1$ is an integer of 0 to $2m_1+4$; $Z^1$ is an alkoxy group, an aryloxy group, a dialkylamino group, a diarylamino group, an alkylarylamino group, an alkylthio group, or an arylthio group, and in a case in which $n_1$ is an integer of 2 or more, such a plurality of $Z^1$'s may be the same as or different from each other; and one bond marked with a symbol ** is formed toward a hydroxyl group, as one subject to which G is bonding, and other bond marked therewith is formed toward a carbon atom having a double bond, as other subject to which G is bonding.

In Formula (a)-1, $m_1$ is an integer of 0 to 2 (0, 1, or 2), and defines the number of ring skeleton(s) included in the aromatic hydrocarbon group. In other words, the aromatic hydrocarbon group in a case in which $m_1$ is 0 is a 1,2-phenylene group, the aromatic hydrocarbon group in a case in which $m_1$ is 1 is a naphthalene-2,3-diyl group, and the aromatic hydrocarbon group in a case in which $m_1$ is 2 is an anthracene-2,3-diyl group.

In Formula (a)-1, $n_1$ is an integer of 0 to $2m_1+4$, and represents the number of bond(s) to the aromatic hydrocarbon group of $Z^1$.

In other words, in a case in which $m_1$ is 0, $n_1$ is an integer of 0 to 4, preferably an integer of 0 to 3, more preferably an integer of 0 to 2, and still more preferably 0 or 1.

In a case in which $m_1$ is 1, $n_1$ is an integer of 0 to 6, preferably an integer of 0 to 4, more preferably an integer of 0 to 3, still more preferably an integer of 0 to 2, and particularly preferably 0 or 1.

In a case in which $m_1$ is 2, $n_1$ is an integer of 0 to 8, preferably an integer of 0 to 4, more preferably an integer of 0 to 3, still more preferably an integer of 0 to 2, and particularly preferably 0 or 1.

In Formula (a)-1, $Z^1$ is an alkoxy group, an aryloxy group, a dialkylamino group, a diarylamino group, an alkylarylamino group, an alkylthio group, or an arylthio group, and is the same as in the substituent included in the aromatic hydrocarbon group or aromatic heterocyclic group in G.

In a case in which $n_1$ is an integer of 2 or more and a plurality of $Z^1$'s are present (the compound (1) has a plurality of $Z^1$'s), such a plurality of $Z^1$'s may be the same as or different from each other. In other words, such $Z^1$'s may be all the same, may be all different, or may be only partially the same.

In a case in which $n_1$ is an integer other than 0, the position of $Z^1$ bonding to the aromatic hydrocarbon group is not particularly limited.

In Formula (a)-1, one bond marked with a symbol  is formed toward a hydroxyl group in the formula (a), as one subject to which G is bonding. Further, other bond marked with a symbol  is formed toward a carbon atom having a double bond in the formula (a), as other subject to which G is bonding.

The first skeleton is, for example, preferably a group represented by the following formula (a)-2. The compound having the first skeleton and the second skeleton preferably generate a base in which a hydrogen atom is bonding with a nitrogen atom of the second skeleton, and coumarin or a coumarin derivative, by light irradiation.

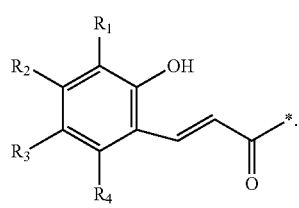

(a)-2

In Formula (a)-2, each of $R_1$ to $R_4$ independently represents a hydrogen atom, the substituent alkyl group, an alkoxy group, an aryloxy group, a dialkylamino group, a diarylamino group, an alkylarylamino group, an alkylcarbonyl group, an arylcarbonyl group, an alkyloxycarbonyl group, an aryloxycarbonyl group, an alkylcarbonyloxy group, an arylcarbonyloxy group, an alkylthio group, an arylthio group, a cyano group (—CN), a halogen atom, a nitro group, a haloalkyl group (halogenated alkyl group), a hydroxyl group (—OH), a mercapto group (—SH), an amino group, the aromatic hydrocarbon group, and the aromatic heterocyclic group, and * represents the bonding position with the nitrogen atom. Two or more of $R_1$ to $R_4$ are optionally bonding to each other to form a ring structure.

The second skeleton preferably has a structure represented by the following formula (1)-12, (1)-13, or (1)-14, and more preferably a structure represented by the following formula (1)-13 or (1)-14.

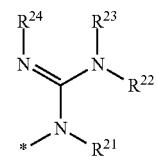

(1)-12

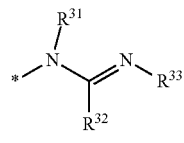

(1)-13

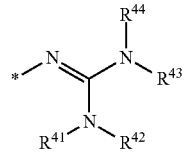

(1)-14

In formula (1)-12 to formula (1)-14, each of $R^{22}$, $R^{23}$, $R^{24}$, $R^{32}$, $R^{33}$, $R^{41}$, $R^{42}$, $R^{43}$, and $R^{44}$ independently represents a hydrogen atom or a hydrocarbon group that may have a substituent; each of $R^{21}$ and $R^{31}$ independently represents a hydrocarbon group that may have a substituent; * represents a bonding position that forms a single bond by combining with * in the formula (a); two or more of $R^{21}$ to $R^{24}$ are optionally bonding to each other to form a ring structure; two or more of $R^{31}$ to $R^{33}$ are optionally bonding to each other to form a ring structure; and two or more of $R^{41}$ to $R^{44}$ are optionally bonding to each other to form a ring structure.

The hydrocarbon group in $R^{21}$ to $R^{24}$, $R^{31}$ to $R^{33}$, and $R^{41}$ to $R^{44}$ may be any of an aliphatic hydrocarbon group or an aromatic hydrocarbon group (aryl group), and may be an aliphatic hydrocarbon group in which one or more hydrogen atoms are substituted with an aromatic hydrocarbon group, or may be a polycyclic hydrocarbon group formed by condensing a cyclic aliphatic hydrocarbon group and an aromatic hydrocarbon group.

The aliphatic hydrocarbon group may be any of a saturated aliphatic hydrocarbon group (alkyl group) or an unsaturated aliphatic hydrocarbon group.

The linear or branched alkyl group preferably has from 1 to 20 carbon atoms, and examples of the linear or branched alkyl group include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a 1-methylbutyl group, a n-hexyl group, a 2-methylpentyl group, a 3-methylpentyl group, a 2,2-dimethylbutyl group, a 2,3-dimethylbutyl group, a n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, a n-octyl group, an isooctyl group, a 2-ethylhexyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group.

The cyclic alkyl group preferably has from 3 to 20 carbon atoms, and examples of the cyclic alkyl group include a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, a 1-adamantyl group, a 2-adamantyl group, and a tricyclodecyl group, and further include such a cyclic alkyl group in which one or more hydrogen atoms are/is substituted with a linear, branched, or cyclic alkyl group. Examples of the linear, branched, or cyclic alkyl group with which hydrogen atom(s) are/is substituted include the above exemplified as alkyl groups.

The unsaturated aliphatic hydrocarbon group may be any of a linear, branched, or cyclic unsaturated aliphatic hydrocarbon group, and may be any of a monocyclic or polycyclic unsaturated aliphatic hydrocarbon group in a case in which the unsaturated aliphatic hydrocarbon group is a cyclic unsaturated aliphatic hydrocarbon group. The unsaturated aliphatic hydrocarbon group preferably has from 2 to 20 carbon atoms.

Examples of the unsaturated aliphatic hydrocarbon group include a group obtained by substituting one or more single bonds (C—C) between carbon atoms in the alkyl group in, for example, with double bond(s) (C=C) or triple bond(s) (C≡C) being unsaturated bond(s).

The number of such unsaturated bond(s) in the unsaturated aliphatic hydrocarbon group may be only one, or two or more, and, in a case where the number is two or more, such unsaturated bonds may correspond to only double bonds or triple bonds, or may correspond to a mixture of a double bond and a triple bond.

The position(s) of the unsaturated bond(s) in the unsaturated aliphatic hydrocarbon group are/is not particularly limited.

Preferable examples of the unsaturated aliphatic hydrocarbon group include an alkenyl group and an alkynyl group which are linear or branched, and cycloalkenyl group and a cycloalkynyl group which are cyclic, each corresponding to the above group having one unsaturated bond.

Examples of the alkenyl group include an ethenyl group (vinyl group), a 2-propenyl group (allyl group), and a cyclohexenyl group.

The aryl group may be any of a monocyclic or polycyclic aryl group, and preferably has from 6 to 20 carbon atoms. Examples of such an aryl group include a phenyl group, a 1-naphthyl group, a 2-naphthyl group, an o-tolyl group, a m-tolyl group, a p-tolyl group, and a xylyl group (dimethylphenyl group), and further include such an aryl group in which one or more hydrogen atoms are/is substituted with such an aryl group or the alkyl group. Such an aryl group having a substituent preferably has from 6 to 20 carbon atoms also including carbon atom(s) of the substituent.

In Formula (1)-12, in a case in which two or more of $R^{21}$, $R^{22}$, $R^{23}$, and $R^{24}$ are hydrocarbon groups, the hydrocarbon groups may be bonding to each other to form a ring together with nitrogen atoms to which the hydrocarbon groups are bonding and a carbon atom (the same carbon atom to which all three nitrogen atoms are bonding) bonding to the nitrogen atoms. The "two or more hydrocarbon groups bonding to each other" refers to, for example, a case in which only two, only three, or all (four) of $R^{21}$ to $R^{24}$ are hydrocarbon groups and only any two or three hydrocarbon groups are bonding to each other and a case in which all (four) of $R^{21}$ to $R^{24}$ are hydrocarbon groups and all the hydrocarbon groups are bonding to each other.

In a case in which two or more hydrocarbon groups are bonding to each other, the position at which carbon atoms are bonding (bonding position) is not particularly limited. For example, in a case in which the bonding hydrocarbon groups are linear or branched, the bonding position may be located on a carbon atom at any end of the hydrocarbon groups, may be located on a carbon atom at any so-called root, included in any of the hydrocarbon groups and directly bonding to any of nitrogen atoms represented in the formula (1)-12, or may be located on a carbon atom between the end and the root. In this regard, in a case in which the hydrocarbon groups bonding are cyclic, or have both a linear structure and a cyclic structure, the bonding position may be located on a carbon atom at the root or on any carbon atom other than such a carbon atom.

In a case in which two hydrocarbon groups of $R^{21}$, $R^{22}$, $R^{23}$, and $R^{24}$ are bonding to each other, a ring formed may be any of a monocyclic or polycyclic ring.

In Formula (1)-13, in a case in which two or more of $R^{31}$, $R^{32}$, and $R^{33}$ are hydrocarbon groups, the hydrocarbon groups may be bonding to each other to form a ring together with nitrogen atoms or a carbon atom, to which the hydrocarbon groups are bonding, and carbon atom bonding to the nitrogen atoms or nitrogen atoms bonding to the carbon atom. The "two or more hydrocarbon groups bonding to each other" means the same as a case in which any hydrocarbon groups of $R^{21}$ to $R^{24}$ are bonding to each other, as described above. For example, such bonding encompasses a case in which only two or all (three) of $R^{31}$ to $R^{33}$ are hydrocarbon groups and only any two hydrocarbon groups are bonding to each other and a case in which all (three) of $R^{31}$ to $R^{33}$ are hydrocarbon groups and all the hydrocarbon groups are bonding to each other, and the way of bonding of the hydrocarbon groups is also the same as in the case of $R^{21}$ to $R^{24}$.

In Formula (1)-14, in a case in which two or more of $R^{41}$, $R^{42}$, $R^{43}$, and $R^{44}$ are hydrocarbon groups, the hydrocarbon groups may be bonding to each other to form a ring together with nitrogen atoms to which the hydrocarbon groups are bonding and a carbon atom (the same carbon atom to which all three nitrogen atoms are bonding) bonding to the nitrogen atoms. The "two or more hydrocarbon groups bonding to each other" means the same as a case in which any hydrocarbon groups of $R^{21}$ to $R^{24}$ are bonding to each other, as described above. For example, such bonding encompasses a case in which only two, only three, or all (four) of $R^{41}$ to $R^{44}$ are hydrocarbon groups and only any two or three hydrocarbon groups are bonding to each other and a case in which all (four) of $R^{41}$ to $R^{44}$ are hydrocarbon groups and all the hydrocarbon groups are bonding to each other, and the way of bonding of the hydrocarbon groups is also the same as in the case of $R^{21}$ to $R^{24}$.

In the structure represented by the aforementioned formula (1)-13, it is preferable that $R^{32}$ is a hydrocarbon group, and $R^{31}$ and $R^{33}$ are hydrocarbon groups (preferably saturated hydrocarbon groups) and are bonding to each other, it is more preferable that $R^{32}$ is a hydrocarbon group, and $R^{31}$ and $R^{33}$ are bonding to each other to form an ethylene group, and it is still more preferable that $R^{32}$ is a methyl group, and $R^{31}$ and $R^{33}$ are bonding to each other to form an ethylene group.

In the structure represented by the aforementioned formula (1)-14, it is preferable that all of $R^{41}$ to $R^{44}$ are hydrocarbon groups, and it is more preferable that all of $R^{41}$ to $R^{44}$ are methyl groups.

Modified Example

The modified example of a photobase generator in the disclosure includes a compound including a first skeleton represented by the above-mentioned formula (a), and a second skeleton that includes a nitrogen atom bonding to a bonding position of the first skeleton to form an amide group and that is represented by the above-mentioned formula (1)-12, (1)-13, or (1)–14, in which the compound is the photobase generator generating a base, in which a hydrogen atom is bonding with the nitrogen atom of the second skeleton, by light irradiation. Regarding the photobase generator of the modified example, the description of the configuration common to the photobase generator in the disclosure described above is omitted, and the differences between the photobase generator in the disclosure described above and the photobase generator of the modified example will be described below.

In the modified example, in a case in which the structure represented by the formula (1)-13 has a ring structure formed by bonding $R^{31}$ and $R^{33}$ to each other, it is preferable that the ring structure does not exhibit aromaticity, it is more preferable that $R^{31}$ and $R^{33}$ are bonding to each other to form a saturated hydrocarbon group, and it is still more preferable that $R^{31}$ and $R^{33}$ are bonding to each other to form an ethylene group.

Photoreactive Composition

The photoreactive composition in the disclosure includes the photobase generator in the disclosure, and the base-reactive compound, in which the base-reactive compound includes a functional group that is converted, by the action of a base, into a group exhibiting reactivity, or includes a group that reacts in response to the action of a base. The compound including the functional group that is converted, by the action of the base, into the group exhibiting reactivity may be a compound including only one functional group described above, may be a compound including two or more functional groups described above, or may be a mixture thereof. The compound including the group that reacts in response to the action of the base may be a compound including only one group that reacts in response to the action of the base, may be a compound including two or more groups that reacts in response to the action of the base, or may be a mixture thereof.

For example, when the photoreactive composition in the disclosure is irradiated with light, a base is generated from the photobase generator, and the functional group, which is included in the base-reactive compound of the photoreactive composition, is converted by the action of the base to exhibit reactivity, or the functional group, which is included in the base-reactive compound, reacts by the action of the base. Thus, the aforementioned photoreactive composition is irradiated with light to generate a base, thereby allowing the base-reactive compound included in the photoreactive composition to be reacted, and the reaction product is obtained.

The photoreactive composition may be a photo curable composition that is to be cured by a reaction of the base-reactive compound by light irradiation, and such a photocurable composition may be used for production of a cured product by light irradiation.

The photoreactive composition may be a photoreactive material (positive type) to be solubilized by light irradiation, or may be a photoreactive material (negative type) to be cured by light irradiation.

The photobase generator which the photoreactive composition in the disclosure includes, may be adopted singly, or in combination of two or more kinds thereof, and in a case of two or more kinds, the combination and the ratio can be arbitrarily set.

According to the photoreactive composition in the disclosure, the content ratio of the photo base generator is preferably from 4% by mass to 39% by mass, more preferably from 6% by mass to 36% by mass, still more preferably from 8% to 33% by mass, with respect to the content ratio of the base-reactive compound. When the content ratio of the photobase generator is 4% by mass or more, the reaction of the base-reactive compound proceeds more easily. When the content of the photobase generator is 39% by mass or less, overuse of the photobase generator is prevented.

Base-Reactive Compound

The photoreactive compound in the disclosure includes the base-reactive compound. The base-reactive compound is the compound (in the disclosure, also referred to as "base-reactive compound (9-2a)") including the functional group that is converted, by the action of the base, into the group exhibiting reactivity, or a compound (in the disclosure, also referred to as "base-reactive compound (9-2b)") including the group that reacts in response to the action of the base. The base-reactive compound 9-2b) differs from the base-reactive compound (9-2a) in that the group that reacts is not converted into a group exhibiting reactivity by the action of the base.

Examples of a reaction that proceeds in the base-reactive compound include addition polymerization and condensation polymerization.

For example, the base-reactive compound may be any of a monomer, an oligomer, and a polymer, or may be either of a low molecule compound or a high molecule compound.

As the base-reactive compound, the known compound can be used, and for example, the base-reactive compound described in "Japanese Patent Application Laid-Open (JP-A) No. 2011-80032" can be used. However, these compounds are just an example.

Examples of the base-reactive compound (9-2a) include a compound in which the functional group is decomposed by the action of the base and converted into a group exhibiting reactivity. Examples of such a base-reactive compound (9-2a) include a compound including a carbonate skeleton (—O—C(=O)—O—), and a photosensitive polyimide.

Examples of the base-reactive compound (9-2b) include an epoxy resin, a silicon resin, an alkoxysilane compound, a (meth)acrylate compound, and a thiol compound.

In the disclosure, "(meth)acrylate" is a concept that includes both "acrylate" and "methacrylate".

The base-reactive compound which the photoreactive composition in the disclosure includes, may be adopted singly, or in combination of two or more kinds thereof, and in a case of two or more kinds, the combination and the ratio can be arbitrarily set.

Other Component

The photoreactive composition in the disclosure may further include any component other than the base-reactive compound, and the photobase generator.

Such other component is not particularly limited and can be arbitrarily selected for any purpose, as long as the effect of the invention is not impaired.

Such other component included in the photoreactive composition may be adopted singly, or in combination of two or more kinds thereof, and in a case of two or more kinds, the combination and the ratio can be arbitrarily set.

Examples of such other component include sensitizers, fillers, pigments, and solvents.

Sensitizer

The photoreactive composition in the disclosure may include a sensitizer.

The sensitizer is not particularly limited and examples thereof include benzophenone, naphthoquinone, anthraquinone, xanthene, thioxanthene, xanthone, thioxanthone, anthracene, phenanthrene, phenanthroline, pyrene, pentacene, and derivatives thereof.

The sensitizer may be adopted singly, or in combination of two or more kinds thereof, and in a case of two or more kinds, the combination and the ratio can be arbitrarily set.

The content of the sensitizer in the photoreactive composition is not particularly limited, and may be adjusted as appropriate.

Filler

The photoreactive composition in the disclosure may include a filler. A filler can be included, thereby allowing characteristics, for example, the viscosity of the photoreactive composition itself, and the strength of the photoreactive composition (reaction product described below) after the reaction to be modulated.

The filler may be any known filler and is not particularly limited. For example, the filler may be any of a fibrous, plate-like, or granular filler, and the shape, the size, and the material thereof may be each appropriately selected for any purpose.

The filler included in the photoreactive composition may be adopted singly, or in combination of two or more kinds thereof, and in a case of two or more kinds, the combination and the ratio can be arbitrarily set.

The content of the filler in the photoreactive composition is not particularly limited and may be appropriately modulated for any purpose.

Pigment

The photoreactive composition in the disclosure may include a pigment. A pigment can be included, thereby allowing, for example, light permeability to be modulated.

The pigment included in the photoreactive composition may be any known pigment such as a white, blue, red, yellow, or green pigment, and is not particularly limited.

The pigment included in the photoreactive composition may be adopted singly, or in combination of two or more kinds thereof, and in a case of two or more kinds, the combination and the ratio can be arbitrarily set.

The content of the pigment in the photoreactive composition is not particularly limited and may be appropriately modulated for any purpose.

Solvent

The photoreactive composition in the disclosure may include a solvent. A solvent can be included, thereby allowing handleability to be enhanced.

The solvent is not particularly limited, and may be appropriately selected in consideration of solubility, stability, and the like of the base-reactive compound and the photobase generator.

The solvent is not particularly limited, and examples thereof include halogenated hydrocarbon such as dichloromethane or chloroform; aromatic hydrocarbon such as toluene, o-xylene, m-xylene, or p-xylene; aliphatic hydrocarbon such as hexane, heptane, or octane; carboxylate ester such as ethyl acetate or butyl acetate; ether such as diethyl ether, tetrahydrofuran (THF), or 1,2-dimethoxyethane (dimethylcellosolve); ketone such as acetone, methyl ethyl ketone (MEK), cyclohexanone, or cyclopentanone; nitrile such as acetonitrile; and amide such as N,N-dimethylformamide (DMF) or N,N-dimethylacetamide.

The solvent included in the photoreactive composition may be adopted singly, or in combination of two or more kinds thereof, and in a case of two or more kinds, the combination and the ratio can be arbitrarily set.

The content of the solvent in the photoreactive composition is preferably from 3 times by mass to 20 times by mass, more preferably from 4 times by mass to 15 times by mass, and still more preferably from 5 times by mass to 10 times by mass with respect to the content of the base-reactive compound. The content of the solvent is in such a range, thereby allowing the photoreactive composition to be more enhanced in handleability.

The photoreactive composition is obtained by blending the base-reactive compound, the photobase generator, and, if necessary, any other component. One obtained after blending of such respective components may be adopted as the photoreactive composition as it is, or may be, if necessary, subsequently subjected to, for example, a known purification operation, thereby obtaining the photoreactive composition.

The blending of such respective components may be performed by adding all the components and then mixing them, performing mixing while sequentially adding some of the components, or performing mixing while sequentially adding all the components.

The mixing method is not particularly limited, and may be appropriately selected from known methods including a method involving mixing under rotation of, for example, a stirring bar or a stirring blade; a method involving mixing by use of, for example, a mixer; and a method involving mixing by addition of ultrasonic wave.

The temperature in the blending is not particularly limited as long as the respective components blended are not degraded, and the temperature can be, for example, from 3° C. to 30° C.

The blending time is also not particularly limited as long as the respective components blended are not degraded, and the time can be, for example, from 30 seconds to 1 hour.

It is noted that these blending conditions are merely examples.

Reaction Product

The reaction product in the disclosure is obtained by reacting the photoreactive composition. The method of producing the reaction product in the disclosure is described in the section of the method of producing a reaction product in the disclosure, described below.

The shape of the reaction product in the disclosure is, for example, a film or a rod shape, and can be arbitrarily selected for any purpose.

(Method of Producing Reaction Product)

The method of producing a reaction product in the disclosure includes a step of irradiating the photoreactive composition with light, thereby generating the base from the photobase generator. In the base-reactive compound included in the photoreactive composition, the functional group included in the base-reactive compound is converted by the action of the base to exhibit reactivity, or the functional group, which is included in the base-reactive compound, reacts by the action of the base generated. Thus, the aforementioned photoreactive composition is irradiated with light to generate the base, thereby allowing the base-reactive compound included in the photoreactive composition to be reacted, and the reaction product is obtained.

The photoreactive composition may be attached to an objective substance according to a known procedure, and then, if necessary, pre-baked (dried), thereby forming a photoreactive composition layer, and the photoreactive composition layer may be irradiated with light.

For example, in a case in which a film-like reaction product is produced, the reaction product may be produced by coating an objective substance with the photoreactive composition by use of any of various coaters such as a spin coater, an air knife coater, a blade coater, a bar coater, a gravure coater, a roll coater, a roll knife coater, a curtain coater, a die coater, a knife coater, a screen coater, a meyer bar coater, and a kiss coater, or a coating unit such as an applicator, or dipping an objective substance in the photoreactive composition, thereby allowing the photoreactive composition to be attached to the objective substance.

For example, in a case in which a film-like or rod-like reaction product is produced, the reaction product may be produced by allowing the photoreactive composition to be attached to an objective substance by use of a printing procedure such as a screen printing method, a flexographic printing method, an offset printing method, an inkjet printing method, a dispenser printing method, a jet dispenser printing method, a gravure printing method, a gravure offset printing method, or a pad printing method.

The pre-baking may be performed in conditions of, for example, from 40° C. to 120° C. and from 30 seconds to 10 minutes, and is not particularly limited.

The wavelength of light with which the photoreactive composition is irradiated is not particularly limited, and may be, for example, any wavelength in the ultraviolet to visible region. The wavelength of light with which the photoreactive composition is irradiated may be 10 nm or more, may be 200 nm or more, or may be 300 nm or more. The wavelength of light with which the photoreactive composition is irradiated may be 600 nm or less, may be 500 nm or less, or may be 400 nm or less.

The illuminance of light with which the photoreactive composition is irradiated is, for example, preferably from 1 mW/cm$^2$ to 100 mW/cm$^2$, more preferably from 5 mW/cm$^2$ to 80 mW/cm$^2$, and still more preferably from 10 mW/cm$^2$ to 60 mW/cm$^2$.

The exposure doses with which the photoreactive composition is irradiated is, for example, preferably from 100 mJ/cm$^2$ to 20000 mJ/cm$^2$, more preferably from 200 mJ/cm$^2$ to 15000 mJ/cm$^2$, and still more preferably from 300 mJ/cm$^2$ to 12000 mJ/cm$^2$.

It is noted that light irradiation conditions here listed are merely examples and are not limited thereto.

Such a reaction product obtained by irradiating the photoreactive composition with light may be further subjected to post-baking (heating treatment after light irradiation).

The post-baking may be performed in conditions of, for example, from 50° C. to 180° C. and from 20 minutes to 2 hours, and is not particularly limited.

The thickness of the reaction product may be appropriately set for any purpose, and is not particularly limited. The thickness of the reaction product is, for example, preferably from 1 μm to 500 μm, and more preferably from 5 μm to 200 μm. A reaction product having such a thickness can be formed by, for example, setting the thickness of the photoreactive composition layer to any thickness equal to or more than the thickness of an objective reaction product.

For example, the ratio of the thickness of the reaction product (thickness of photoreactive composition layer after light irradiation) with respect to the thickness of the photoreactive composition layer (thickness of photoreactive composition layer before light irradiation) ([thickness of photoreactive composition layer after light irradiation]/[thickness of photoreactive composition layer before light irradiation]) can be, for example, from 0.2 to 1.0, and can be any of from 0.3 to 1.0, from 0.4 to 1.0, from 0.5 to 1.0, from 0.6 to 1.0, from 0.7 to 1.0, from 0.8 to 1.0, or from 0.9 to 1.0, by further modulation of reaction conditions.

EXAMPLES

Hereinafter, the invention will be more specifically described with reference to Examples, but the invention is not limited by these Examples.

Production of Compound (1)-1

Firstly, a compound (X) was reacted with thionyl chloride and 1,1,3,3-tetramethylguanidine in that order to produce a compound (Y).

In practice, a liquid mixture of compound (X) (2.1 g, 0.020 mol) and thionyl chloride (SOCl2, 10 mL) was stirred at room temperature for 7 hours, and then dried dichloromethane (20 mL) and a liquid mixture of 1,1,3,3-tetramethylguanidine (2.3 g, 0.022 mol) and dry dichloromethane (15 mL) were added to this liquid mixture, and the thus-obtained liquid mixture was stirred at 0° C. for 2 hours to perform the reaction.

Next, a saturated aqueous sodium chloride solution was added to the reaction solution, and the reaction solution was washed by shaking in a separating funnel. The washing with this saturated aqueous sodium chloride solution was performed once more, and a total of twice.

As a result, the compound (Y) was obtained as a viscous yellow liquid (yield 94%).

Regarding the obtained compound (Y), the analysis results of $^1$H-NMR, $^{13}$C-NMR, and ESI-MS are shown in Table 1.

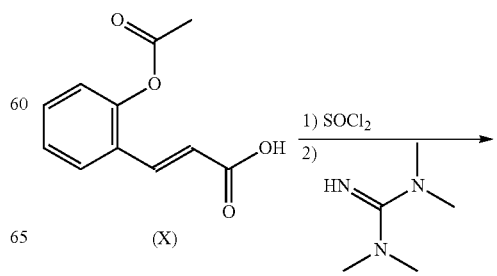

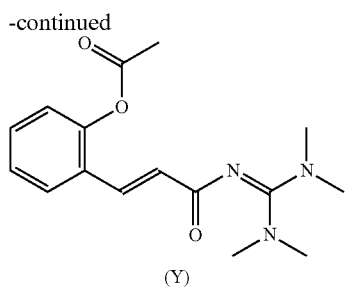

(Y)

TABLE 1

| $^1$H-NMR [δ/ppm]<br>(CDCl$_3$, 300 MHz) | 2.25 (s, 3H, —COCH$_3$)<br>2.81 (s, 12H, —N(CH$_3$)$_2$)<br>6.42 (d, 1H, J = 16 Hz, —C$\underline{H}$=CH—CO—)<br>7.3-7.5 (m, 4H•Ar—H)<br>7.64 (d, 1H, J = 16 Hz, —CH=C$\underline{H}$—CO—) |
|---|---|
| $^{13}$C-NMR [δ/ppm]<br>(CDCl$_3$, 75 MHz) | 21, 40 (sp$^3$) 123, 126, 127, 128, 1$\overline{29}$, 132, 149 (sp$^2$),<br>168, 169, 172 (C=O, C=N) |
| ESI-Positive-HR<br>[M + H]$^+$ | Calculated value: 326.14806<br>Measured value: 326.14774<br>(Estimated composition formula: C$_{16}$H$_{22}$N$_3$O$_3$)<br>Mass difference: 0.09 mmu |

Next, the compound (Y) was hydrolyzed by the reaction shown below to produce a compound (1)-1.

In practice, a liquid mixture of water (10 mL) and potassium carbonate (0.19 g, 1.5 mmol) was added to a liquid mixture of compound (Y) (0.31 g, 1.2 mmol) and methanol (20 mL), and the reaction was carried out by stirring for 3 hours while heating. After completion of the reaction, the reaction solution was quenched with a saturated ammonium chloride solution.

Next, dichloromethane was added to the thus-obtained reaction solution, and the reaction solution was washed by shaking in a separating funnel. The washing with dichloromethane was performed twice more, and a total of three times.

As a result, the target compound (1)-1 was obtained as a viscous yellow liquid (yield 82%).

Regarding the obtained compound (1)-1, the analysis results of $^1$H-NMR, and $^{13}$C-NMR are shown in Table 2. The pKa of a conjugate acid of 1,1,3,3-tetramethylguanidine generated by light irradiation is 15.2 in water.

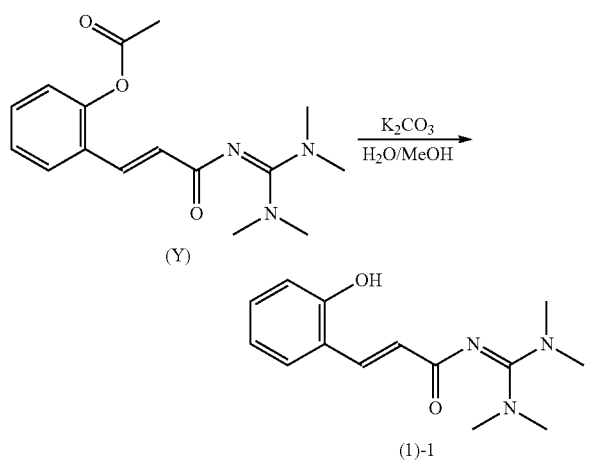

TABLE 2

| $^1$H-NMR [δ/ppm]<br>(d$_6$-CDCl$_3$, 300 MHz) | 2.81 (s, 12H, —N(CH$_3$)$_2$)<br>6.42 (d, 1H, J = 16 Hz, —C$\underline{H}$=CH—CO—)<br>7.3-8.2 (m, 4H•Ar—H)<br>6.65 (d, 1H, J = 16 Hz, —CH=C$\underline{H}$—CO—)<br>10.0 (br, 1H, —OH) |
|---|---|
| $^{13}$C-NMR [δ/ppm]<br>(d$_6$-CDCl$_3$, 75 MHz) | 31 (sp$^3$) 115, 119, 122, 127, 128, 130,<br>134, 156 (sp$^2$), 165, 172 (C=O, C=N) |
| ESI-Positive-HR<br>[M + H]$^+$ | Calculated value: 262.15555<br>Measured value: 262.15557<br>(Estimated composition formula: C$_{14}$H$_{20}$N$_3$O$_2$)<br>Mass difference: 0.02 mmu |

Production of Compound (2)-1

As shown below, a compound (2)-101 was reacted with 1,1,3,3-tetramethylguanidine to produce a compound (2)-1 as an ionic photobase generator.

In practice, a liquid mixture of 1,1,3,3-tetramethylguanidine (2.3 g, 0.022 mol) and dried tetrahydrofuran (10 mL) was added to a liquid mixture of the compound (2)-1 (0.58 g, 0.024 mol) and dried tetrahydrofuran (20 mL), and the thus-obtained liquid mixture was stirred at 0° C. for 2 hours to perform the reaction.

Next, dichloromethane was added to the thus-obtained reaction solution, and the reaction solution was washed by shaking in a separating funnel. The washing with dichloromethane was performed twice more, and a total of three times.

As a result, the target compound (2)-1 was obtained as a yellow solid (yield 90%, acid:base=1.2:1.0).

Regarding the obtained compound (2)-1, the analysis result of $^1$H-NMR is shown in Table 3.

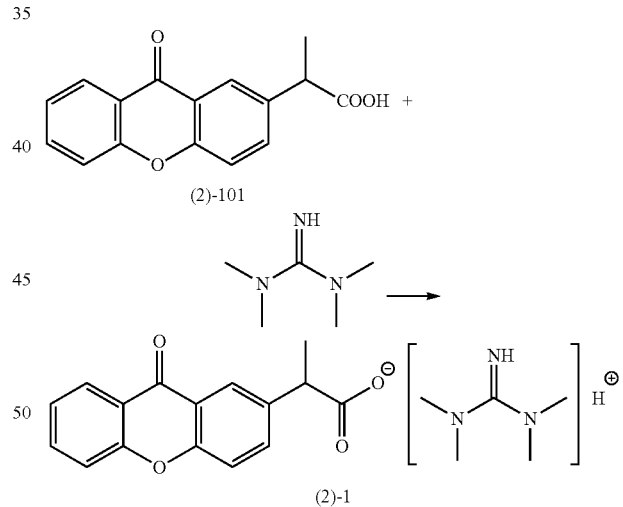

TABLE 3

| $^1$H-NMR [δ/ppm]<br>(CDCl$_3$, 300 MHz) | 1.51 (d, J = 7.5 Hz, 3H, —CH$_3$)<br>2.86 (s, 10H, TMG-H)<br>3.72 (q, J = 7.5 Hz, 1H, —CHCOO)<br>7.3-8.3 (m, 7H, Ar—H) |
|---|---|

Preparation of Compound (3)-1

The following compound (3)-1 as an ionic photobase generator was prepared.

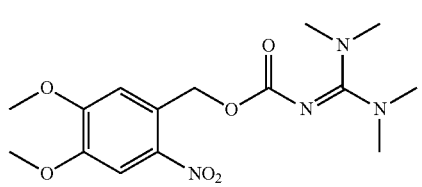

Preparation of Compound (4)-1

The following compound (4)-1 as a non-ionic photobase generator was prepared. The pKa of a conjugate acid of piperidine generated by light irradiation is 11.2 in water.

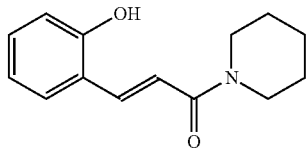

Test Example 1

(Confirmation of Behavior of Compound (1)-1 in Solvent under Light Irradiation with a Wavelength of 365 nm)

The above-obtained compound (1)-1 was dissolved in methanol so as to have a concentration of $2.5 \times 10^{-5}$ mol/L. Then, using an LED lamp, the illuminance was set to 50 mW/cm$^2$, the exposure dose was set to 0, 50, 150 or 300 mJ/cm$^2$, and the obtained methanol solution was irradiated with light having a wavelength of 365 nm. Then, the absorbance of the compound (1)-1 was measured. The results are shown in FIG. 1.

Test Example 2

(Confirmation of Behavior of Compound (1)-1 in the Solvent under Light Irradiation with a Wavelength of 313 nm)

Figure 2:
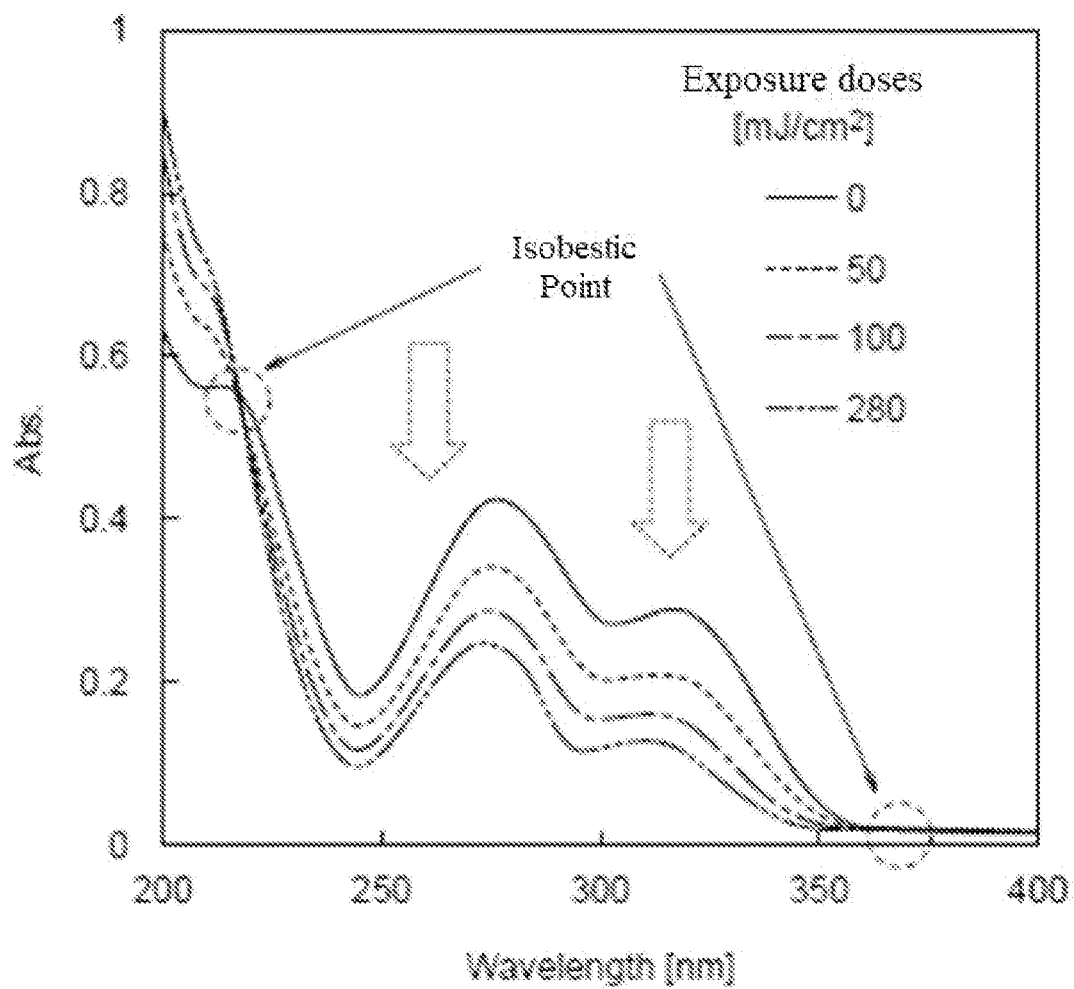
FIG. 2 is a data that illustrates the measurement result of the absorbance of a compound (1)-1 in Test Example 2.

The above-obtained compound (1)-1 was dissolved in methanol so as to have a concentration of $2.5 \times 10^{-5}$ mol/L. Then, using a mercury xenon lamp, the illuminance was set to 50 mW/cm$^2$, the exposure dose was set to 0, 50, 100 or 280 mJ/cm$^2$, and the obtained methanol solution was irradiated with light having a wavelength of 313 nm. Then, the absorbance of the compound (1)-1 was measured. The results are shown in FIG. 2.

In Test Example 1, the molar absorption coefficient was $\varepsilon_{365}=3.1 \times 10^3$ L/(mol cm), and in Test Example 2, the molar absorption coefficient was $\varepsilon_{313}=1.6 \times 10^4$ L/(mol cm).

As is clear from FIG. 1 and FIG. 2, as compared with the spectrum in the case of the exposure doses of 0 mJ/cm$^2$, that is, the spectrum in the case of no light irradiation, in the spectrum for other doses, both increasing peak and decreasing peak exist, and from this measurement result, it was confirmed that the base was generated from the compound (1)-1 in the reaction shown below by light irradiation. Further, it was confirmed that there was no significant difference in the exposure amount for decomposing the compound (1)-1 by light irradiation at 365 nm and 313 nm.

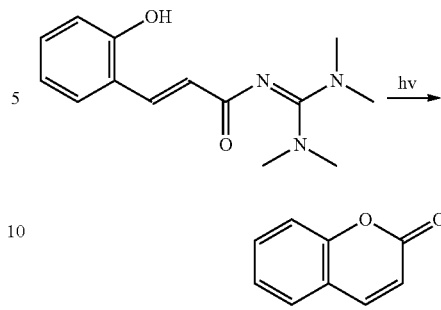

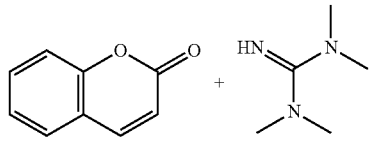

Test Example 3

(Preservation Stability of Compound (1)-1)

A base-reactive compound (9)-301 (0.10 g) as shown below, the compound (1)-1 (0.012 g, 8 molar % with respect to the methoxy group in the base-reactive compound), and methanol (0.51 g) were added in a glass bottle to prepare a liquid mixture.

The liquid mixture was stored in a dark place at 25° C. for 6 days. After storage for 6 days, the glass bottle was shaken or inverted to confirm that the liquid mixture in the glass bottle was liquid.

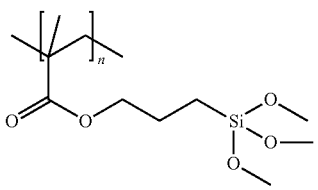

Test Example 4

(Preservation Stability of Compound (2)-1)

The base-reactive compound (9)-301 (0.10 g), the compound (2)-1 (0.013 g, 8 molar % with respect to the methoxy group in the base-reactive compound), and methanol (0.50 g) were added in a glass bottle to prepare a liquid mixture.

The liquid mixture was stored in a dark place at 25° C. for 4 days. After storage for 4 days, the glass bottle was shaken or inverted to confirm that the liquid mixture in the glass bottle was gelled.

From the results of Test Example 3 and Test Example 4, it was assumed that while the cross-linking reaction of the base-reactive compound (9)-301 was suppressed in the mixed solution including the compound (1)-1, the cross-linking reaction of the base-reactive compound (9)-301 was proceeding in the mixed solution including the compound (2)-1.

From the above, it was shown that the composition including the compound (1)-1 and the base-reactive compound (9)-301 was more excellent in preservation stability in the dark than the composition including the compound (2)-1 and the base-reactive compound (9)-301.

Test Example 5

(Outgas Confirmation Test of Compound (1)-1)

Triglycidyl isocyanurate (0.041 g), the compound (1)-1 (0.020 g), and methanol (0.097 g) were blended and stirred at 25° C. for 1 minute to obtain a resin composition for the test.

Next, the resin composition for the test obtained above was applied onto a calcium fluoride plate, a calcium fluoride plate was placed on the obtained coating film, and the coating was sandwiched with the two calcium fluoride plates to produce a laminated body. Using an LED lamp, the illuminance was set to 50 mW/cm$^2$, and the coating film of the laminated body was irradiated with light having a wavelength of 365 nm. At this time, the exposure doses (mJ/cm$^2$) were set to 10,000 mJ/cm$^2$.

After light irradiation, the appearance of the laminated body was confirmed, and it was confirmed whether outgas was generated.

In Test Example 5, a transparent film was obtained between the calcium fluoride plates by light irradiation, and no outgas generation was confirmed as shown in the following reaction formula.

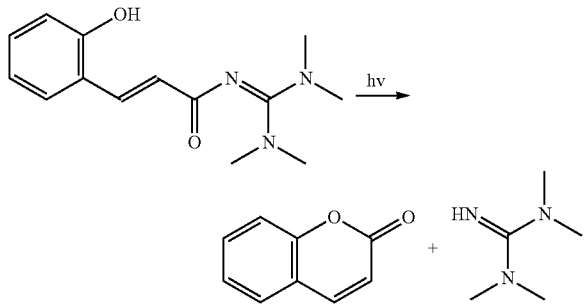

Test Example 6

(Outgas Confirmation Test of Compound (3)-1)

Triglycidyl isocyanurate (0.055 g), the compound (3)-1 (0.032 g), and chloroform (0.080 g) were blended and stirred at 25° C. for 1 minute to obtain a resin composition for the test.

Next, a laminated body was produced and the laminated body was irradiated with light in the same manner as in Test Example 5. After light irradiation, the appearance of the laminated body was confirmed, and it was confirmed whether outgas was generated.

In Test Example 6, the film between the calcium fluoride plates turned yellow due to light irradiation, and bubbles were confirmed. Therefore, in Test Example 6, it was assumed that carbon dioxide was generated as outgas as shown in the following reaction formula. Further, it was assumed that the reason why the film turned yellow in Test Example 6 was that a nitroso group derived from a nitro group was generated.

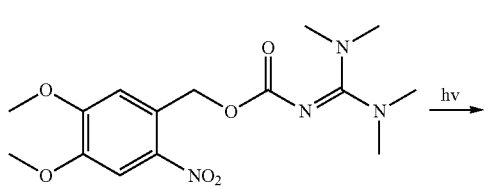

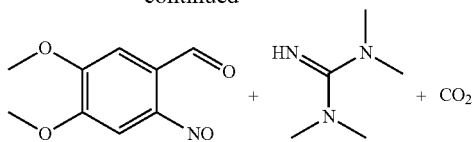

Example 1

(Production of Photoreactive Composition)

The aforementioned base-reactive compound (9)-301 (0.24 g), the compound (1)-1 (7 mol % with respect to the methoxy group in the base-reactive compound), and methanol (1.2 g) were blended and stirred at 25° C. for 1 minute to obtain a photoreactive composition.

(Production of Reaction Product)

The photoreactive composition obtained above was applied onto a silicon wafer by a spin coating method under the conditions of 1000 rpm and 10 seconds. Next, this coating film (photoreactive composition layer) was heated (prebaked) at 60° C. for 1 minute, and then using a mercury xenon lamp, the illuminance was set to 50 mW/cm$^2$, and the coating film was irradiated with light having a wavelength of 313 nm. Three types of coating films in which exposure doses were adjusted to 1000 mJ/cm$^2$ were prepared and heated (post-baked) at 60° C., 80° C. or 100° C. for 30 minutes, respectively. From the above, it was attempted to finally make the three types of coating films into reaction products obtained by polymerizing the base-reactive compound (9)-301.

Comparative Example 1

(Production of Photoreactive Composition)

The aforementioned base-reactive compound (9)-301 (0.24 g), the compound (4)-1 (0.016 g, 7 mol % with respect to the methoxy group in the base-reactive compound), and methanol (1.2 g) were blended and stirred at 25° C. for 1 minute to obtain a photoreactive composition.

(Production of Reaction Product)

The same operation as in Example 1 was performed, and it was attempted to finally make the three types of coating films into reaction products obtained by polymerizing the base-reactive compound (9)-301.

Figure 3:
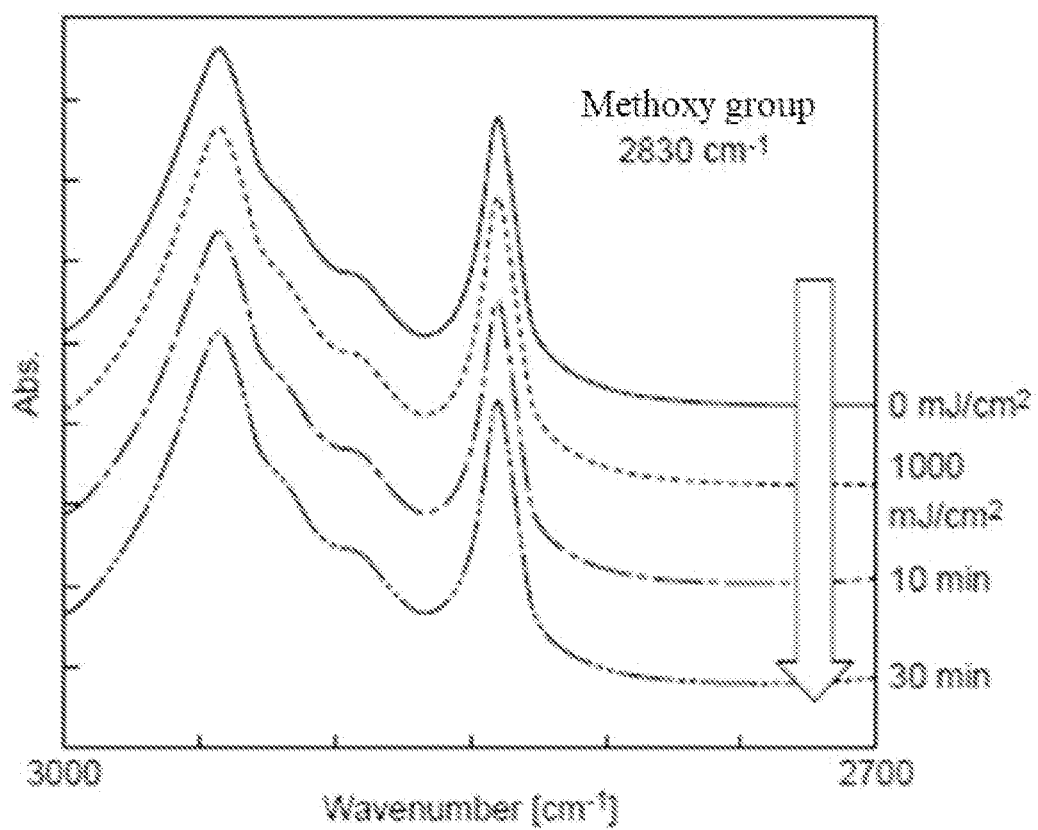
FIG. 3 is a data that illustrates the measurement result of IR spectra of a base-reactive compound (9)-301 in Comparative Example 1.

In Comparative Example 1, regarding the coating film before light irradiation, the coating film after light irradiation, the coating film heated for another 10 minutes after light irradiation, and the coating film heated for another 30 minutes after light irradiation, the peak intensity (2830 cm$^{-1}$) derived from the CH expansion and contraction vibration of the methoxy group was measured with a Fourier transform infrared spectrophotometer (FT-IR). The results are shown in FIG. 3.

Figure 4:
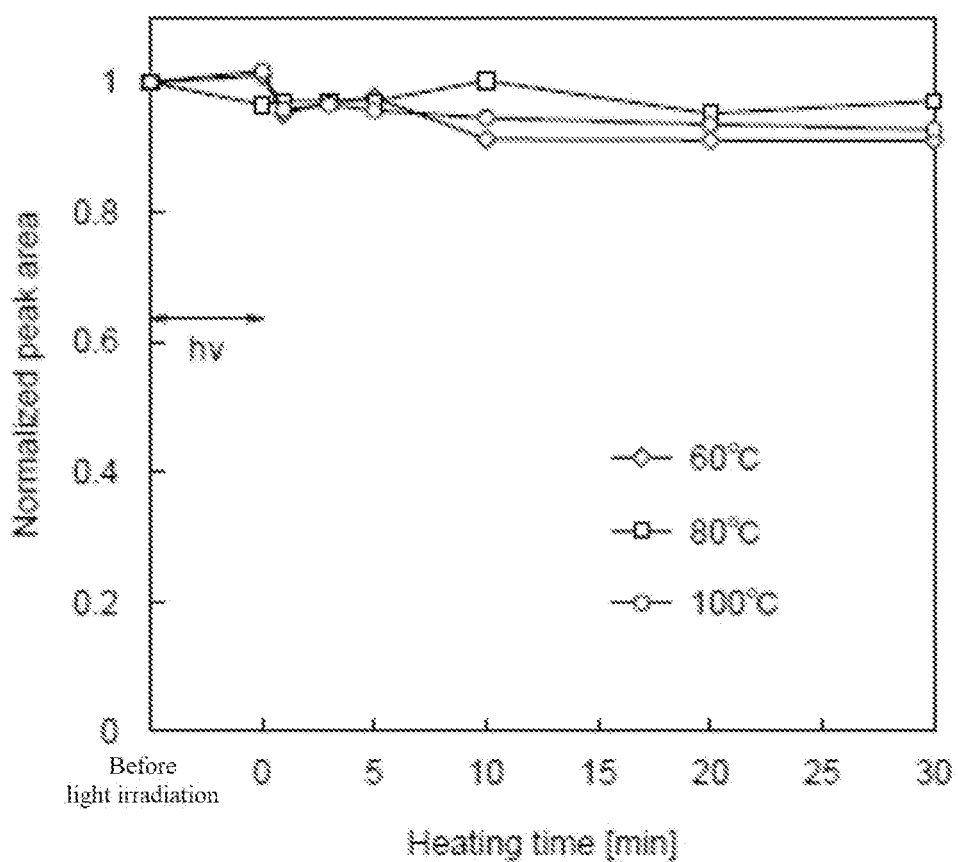
FIG. 4 is a graph illustrating the relationship between the heating time and the peak areas derived from a methoxy group under the light irradiation condition in Comparative Example 1.

Further, in Comparative Example 1, when the coating films before light irradiation were irradiated with light under the conditions of the illuminance 50 mW/cm$^2$, exposure doses 1000 mJ/cm$^2$ and wavelength 313 nm, and then heated at 100° C. for 0 to 30 minutes, the relationship between the heating time and the peak area of the methoxy group is shown in FIG. 4.

Figure 5:
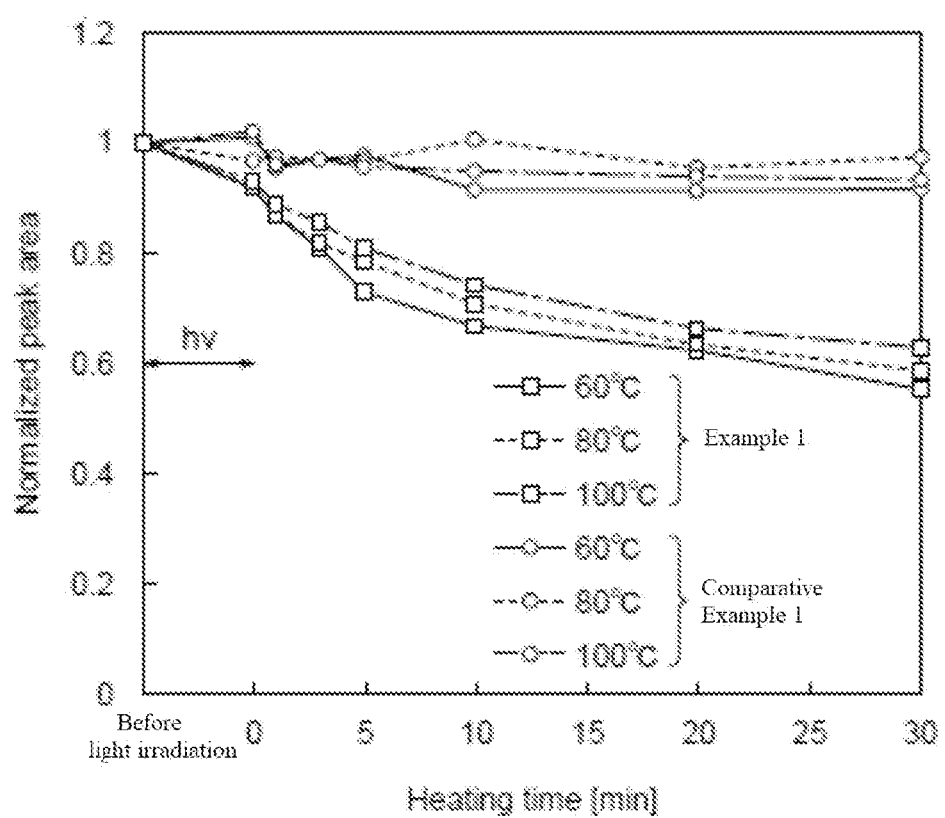
FIG. 5 is a graph illustrating the relationship between the heating time and the peak areas derived from a methoxy group under the light irradiation condition in Example 1 and Comparative Example 1.

In Example 1 and Comparative Example 1, when the coating films before light irradiation were irradiated with light under the conditions of the illuminance 50 mW/cm$^2$, exposure doses 1000 mJ/cm$^2$ and wavelength 313 nm, and then heated at 100° C. for 0 to 30 minutes, the relationship between the heating time and the peak area of the methoxy group is shown in FIG. 5.

Further, in Example 1 and Comparative Example 1, the pencil hardness of the reaction product obtained by heating the coating films after light irradiation at 60° C., 80° C. or 100° C. for 30 minutes were determined. The results are shown in FIG. 6.

From FIG. 3 and FIG. 4, it was confirmed in Comparative Example 1 that the methoxy group in the coating film was slightly reduced by light irradiation on the coating film and heating. Further, from FIG. 5, the reduction rate of the methoxy group in Example 1 is larger than that in Comparative Example 1 by irradiating the coating film with light and heating, that is, the reactivity of the base-reactive compound (9)-301 is excellent. Further, from FIG. 5, it was confirmed that the reduction rate of the methoxy group differed depending on the presence or absence of light irradiation on the coating film and the degree of heating of the coating film.

Figure 6:
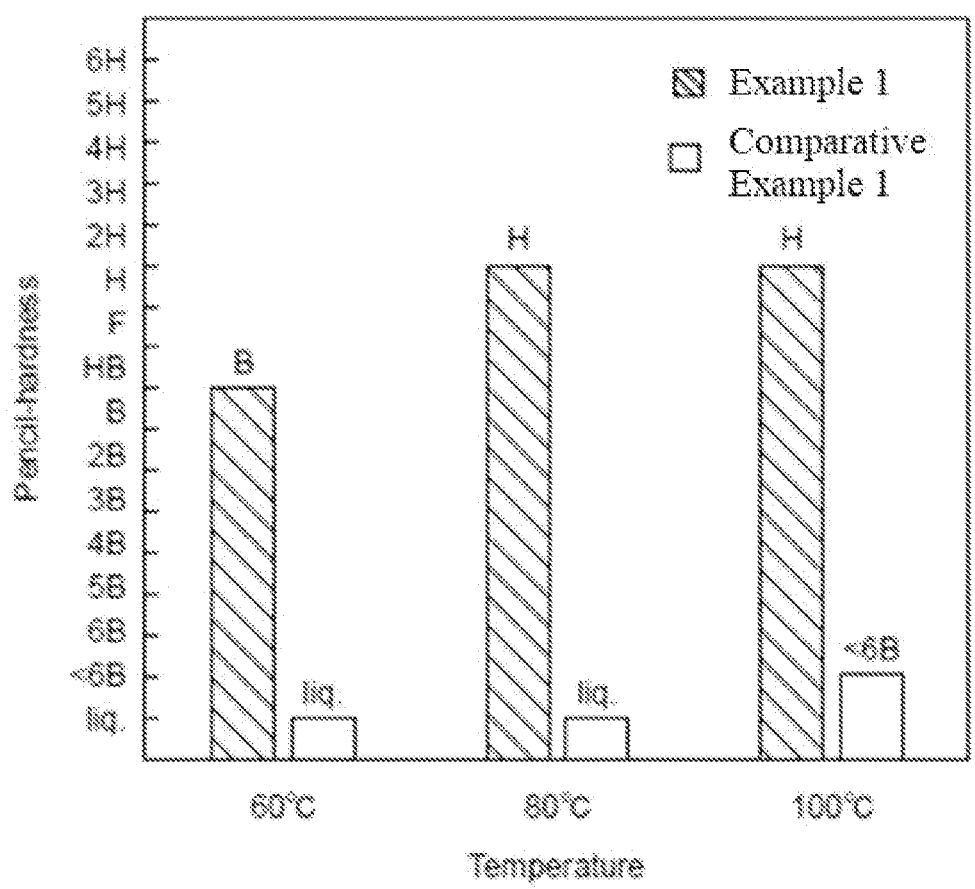
FIG. 6 is a graph illustrating the relationship between the heating temperature and the pencil hardness of the obtained cured product in Example 1 and Comparative Example 1.

As shown in FIG. 6, in Comparative Example 1, the coating film after heating was liquid, and the pencil hardness of the reaction product could not be measured, or the pencil hardness of the reaction product after heating was less than 6B.

On the other hand, in Example 1, it was confirmed that the pencil hardness of the reaction product after heating was B or higher, and that the cured product excellent in the pencil hardness was obtained as the reaction product.

Example 2

(Production of Photoreactive Composition)

Trimethylolpropane triacrylate (0.14 g), the following mentioned base-reactive compound (9)-401 (0.28 g, a ratio of the mercapto group with respect to the acryloyl group in trimethylolpropane triacrylate: 100 mol %), the compound (1)-1 (0.013 g, 10 mol % with respect to trimethylolpropane triacrylate), and methanol (0.43 g) were blended and stirred at 25° C. for 1 minute to obtain a photoreactive composition.

(9)-401

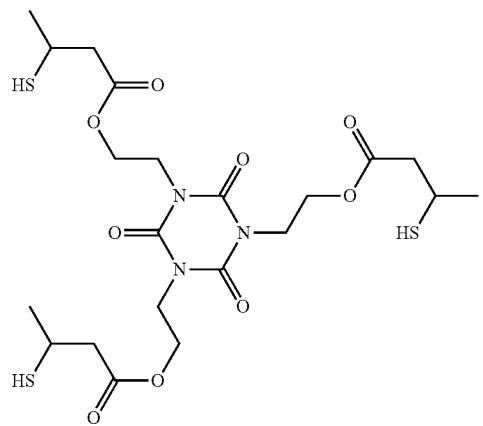

(Production of Reaction Product)

The photoreactive composition obtained above was applied onto a calcium fluoride plate by a spin coating method under the conditions of 1000 rpm and 10 seconds. Next, this coating film (photoreactive composition layer) was heated (prebaked) at 60° C. for 1 minute, and then using an LED lamp, the illuminance was set to 50 mW/cm$^2$, and the coating film was irradiated with light having a wavelength of 365 nm. Exposure doses were adjusted to 1000 mJ/cm$^2$. From the above, it was attempted that a thiorate anion was generated from the compound (9)-401 by the action of the base generated, by light irradiation, from the compound (1)-1, and that a reaction product was produced by a cross-linking reaction of the generated thiorate anion and trimethylolpropane triacrylate.

Figure 7:
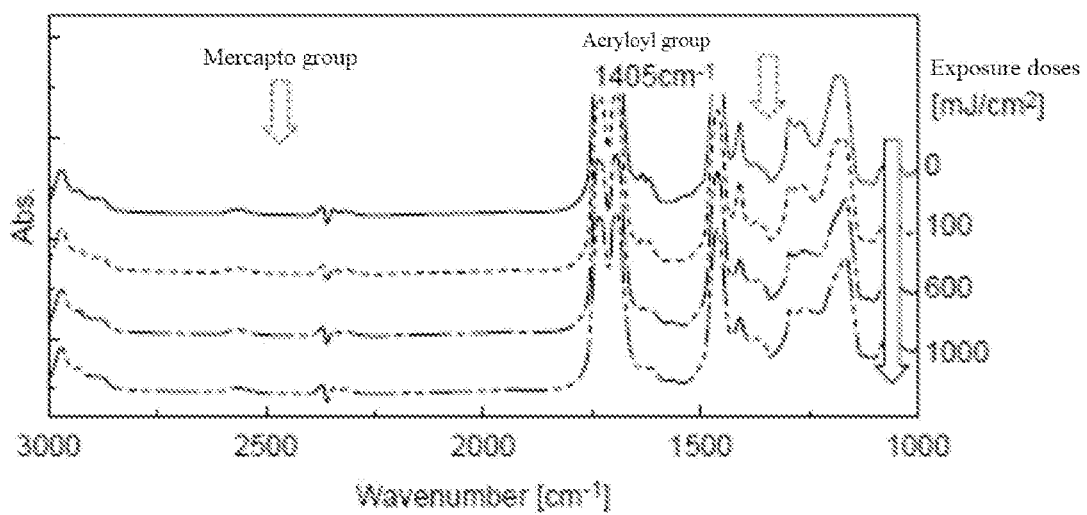
FIG. 7 is a graph illustrating the relationship between the exposure doses to the photoreactive composition and the peak areas derived from an acryloyl group in IR spectra in Example 2.

In Example 2, for the coating film before light irradiation and the coating films in which the exposure doses were adjusted to 0, 100, 600 and 1000 mJ/cm$^2$, the peak intensity (1405 cm$^{-1}$) derived from the stretching vibration of C=C of the acryloyl group was measured with the Fourier transform infrared spectrophotometer (FT-IR). The results are shown in FIG. 7. From FIG. 7, it is shown that the peak area of 1405 cm$^{-1}$ is reduced by the light irradiation, and the consumption of the acryloyl group was confirmed by the light irradiation of 365 nm.

Example 3

In Example 3, a photoreactive composition was produced in the same manner as in Example 2 except that the coating film was irradiated with light of 313 nm using a mercury xenon lamp instead of irradiating the coating film with light of 365 nm using an LED lamp. Further, it was attempted to produce a reaction product.

In Example 3, as in Example 2, the peak intensity was measured with the Fourier transform infrared spectrophotometer (FT-IR), and the change in the peak area of the acryloyl group by light irradiation and the change in the peak area of the mercapto group by light irradiation were evaluated. The results are shown in FIG. 8 and FIG. 9.

Figure 8:
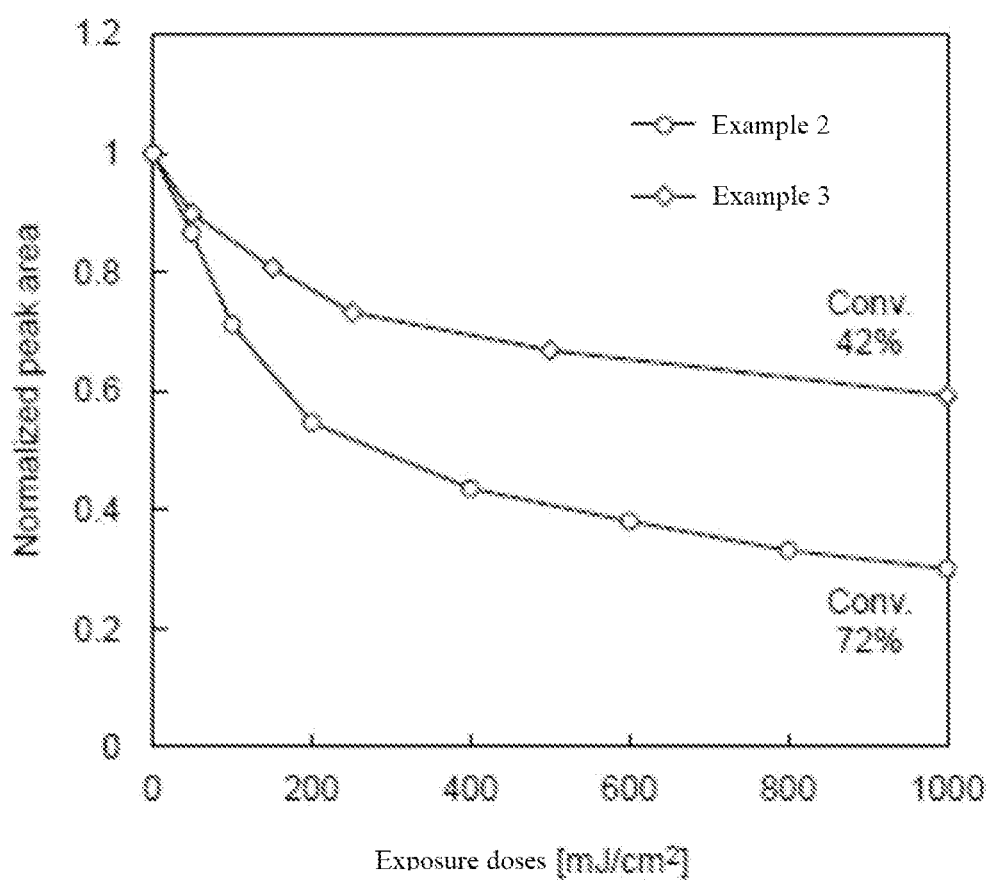
FIG. 8 is a graph illustrating the relationship between the heating time and the peak areas derived from an acryloyl group under the light irradiation condition in Example 2 and Example 3.
Figure 9:
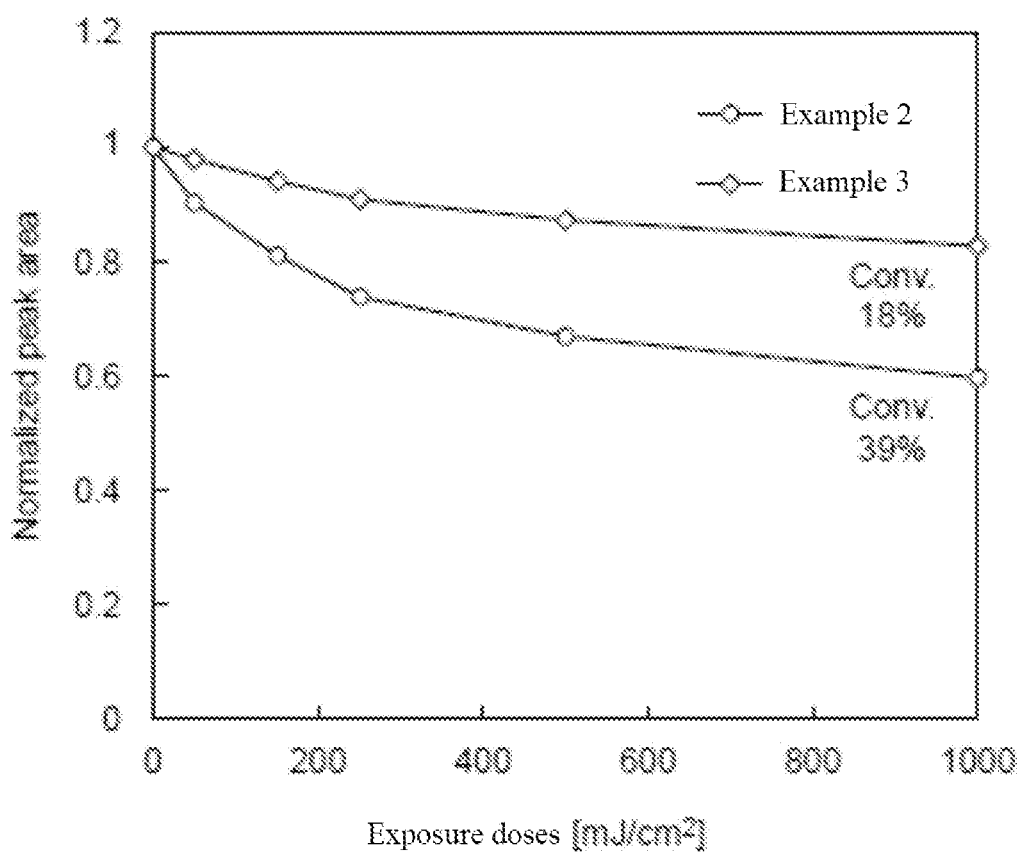
FIG. 9 is a graph illustrating the relationship between the heating time and the peak areas derived from a mercapto group under the light irradiation condition in Example 2 and Example 3.

As shown in FIG. 8 and FIG. 9, it was found that the acryloyl group and the mercapto group were consumed by the light irradiation of the coating film and the cross-linking reaction was proceeding. Further, it was found that in Example 2 in which the coating film was irradiated with light of 365 nm, the crosslinking reaction was more advanced than in Example 3 in which the coating film was irradiated with light of 313 nm. It is assumed that by irradiating the coating film with high-wavelength light, the chemical equilibrium shifts to the cis form of compound (1)-1 in the coating film, and the cyclization reaction that generates the base tends to proceed easily.

Example 4

(Production of Photoreactive Composition)

A bisphenol A type epoxy compound shown in the following structure (JER-828, Mitsubishi Chemical Corporation, 0.19 g), the following compound (9)-501 (0.19 g, a ratio of the mercapto group with respect to the epoxy group in the bisphenol A type epoxy compound: 50 mol %), the compound (1)-1 (0.013 g, 3 mol % with respect to an epoxy group in the bisphenol A type epoxy compound), and cyclopentanone (0.052 g) were blended and stirred at 25° C. for 1 minute to obtain a photoreactive composition.

JER-828

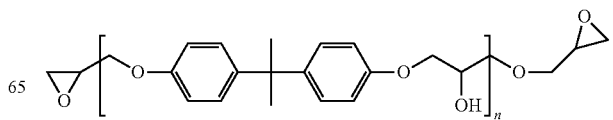

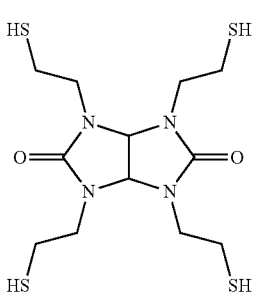

(9)-501

(Production of Reaction Product)

The photoreactive composition obtained above was applied onto a calcium fluoride plate by a spin coating method under the conditions of 1000 rpm and 10 seconds. Next, using an LED lamp, the illuminance was set to 50 mW/cm², and the coating film was irradiated with light having a wavelength of 365 nm. Exposure doses were adjusted to 1000 mJ/cm². Then, the coating film was heated at 60° C. for 30 seconds. From the above, it was attempted that a thiorate anion was generated from the compound (9)-501 by the action of the base generated, by light irradiation, from the compound (1)-1, and that a reaction product was produced by a cross-linking reaction of the generated thiorate anion and the bisphenol A type epoxy compound.

Figure 10A:
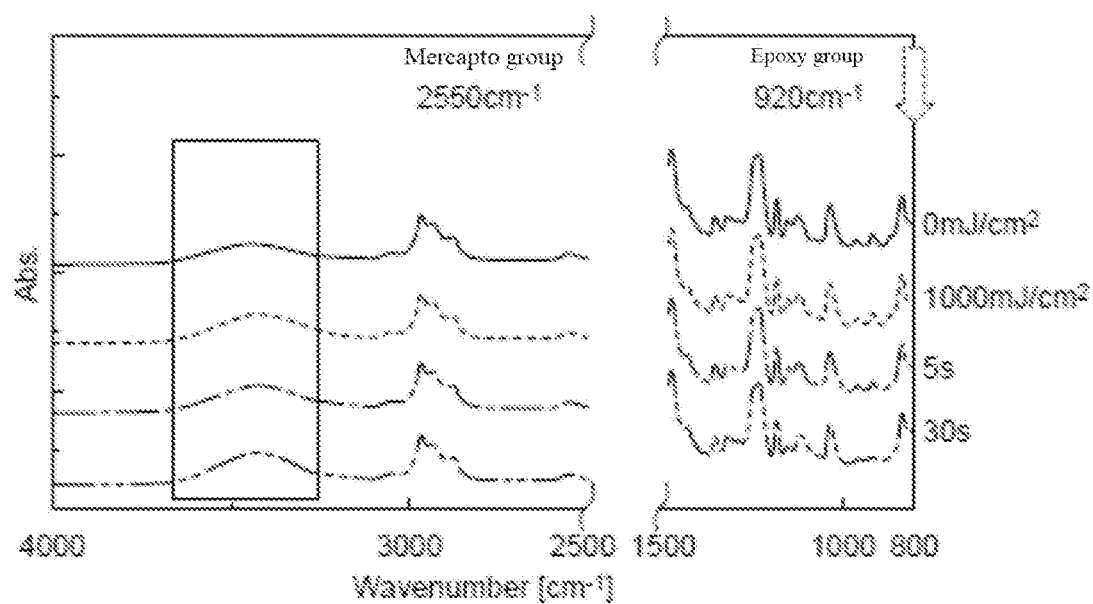
FIG. 10A is a graph illustrating the relationship between the exposure doses to the photoreactive composition and the heating time of the photoreactive composition, and the peak areas derived from an epoxy group and a mercapto group in Example 4.
Figure 10B:
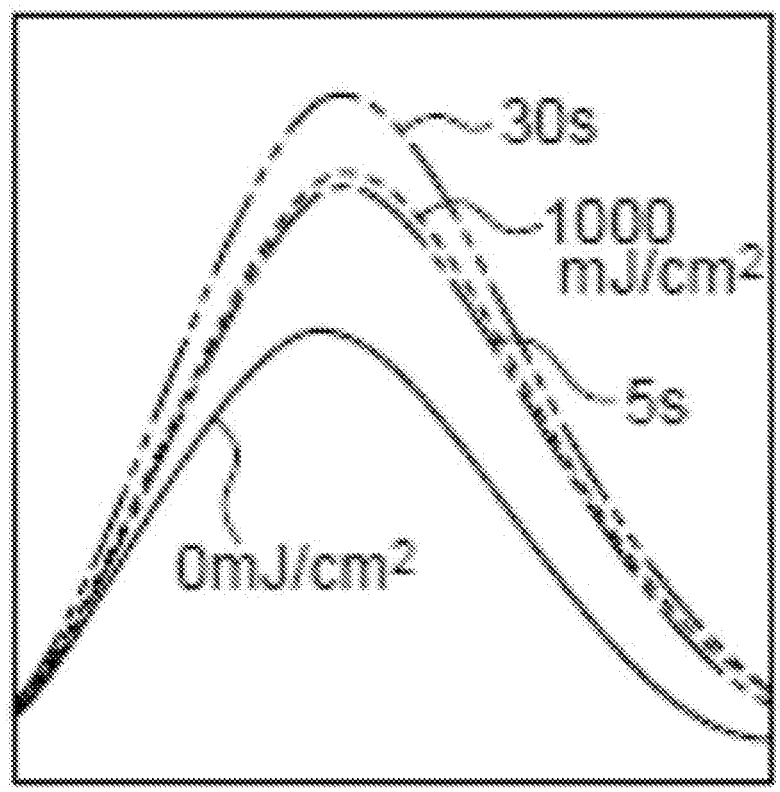
FIG. 10B is a drawing that enlarges a part corresponding to the peak areas derived from a hydroxyl group in FIG. 10A and compares the peak areas derived from a hydroxyl group in each condition.

In Example 4, for the coating film before light irradiation, the coating film after light irradiation, the coating film heated for 5 seconds after light irradiation and the coating film heated for 30 seconds after light irradiation, the peak intensity (920 cm⁻¹) derived from the stretching vibration of C—O of the epoxy group, the peak intensity (2550 cm⁻¹) derived from the stretching vibration of S—H of the mercapto group, and the peak intensity (3600 cm⁻¹) derived from the stretching vibration of O—H of the hydroxyl group were measured with the Fourier transform infrared spectrophotometer (FT-IR). The results are shown in FIG. 10. From FIG. 10, the consumption of the epoxy group and the mercapto group and the increase in the hydroxyl group were confirmed by the light irradiation of 365 nm and thereby, the cross-linking reaction could be confirmed.

In Example 4, for the coating films heated for 0 to 30 seconds without light irradiation, the peak intensity of each functional group was measured with the Fourier transform infrared spectrophotometer (FT-IR) in the same way as above, and the change in the peak area of the epoxy group by light irradiation and the change in the peak area of the mercapto group by light irradiation were evaluated. The results are shown in FIG. 11 and FIG. 12.

Figure 11:
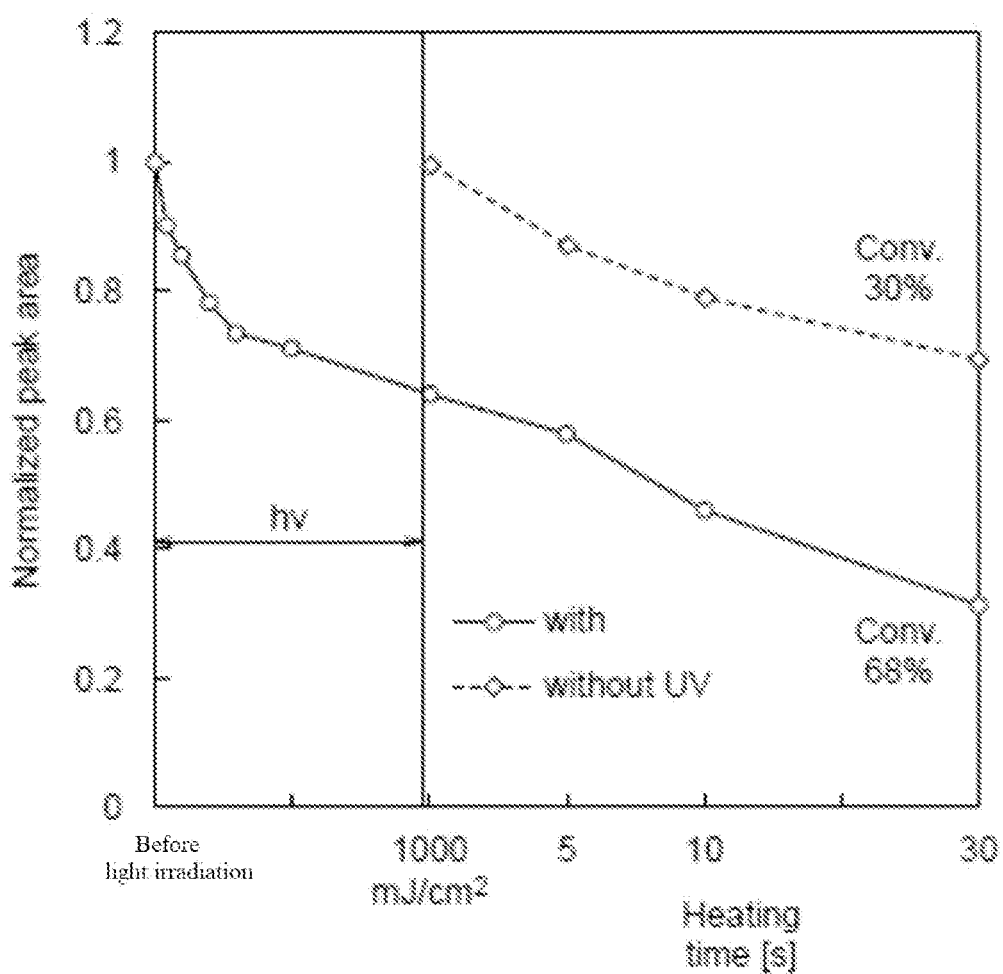
FIG. 11 is a graph illustrating the relationship between the heating time and the peak areas derived from an epoxy group under the light irradiation condition and the light non-irradiation condition in Example 4.
Figure 12:
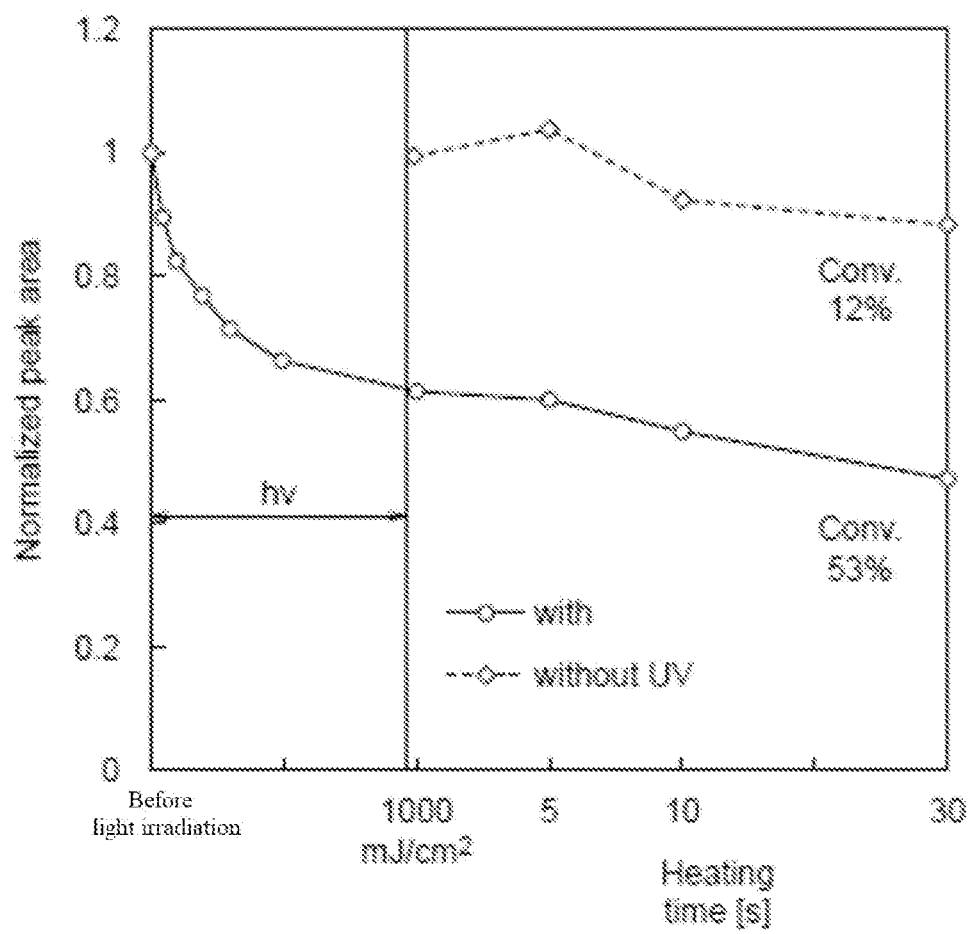
FIG. 12 is a graph illustrating the relationship between the heating time and the peak areas derived from a mercapto group under the light irradiation condition and the light non-irradiation condition in Example 4.

As shown in FIG. 11 and FIG. 12, it was found that, in a case in which the coating films were irradiated with light, the epoxy group and the mercapto group were more consumed and the crosslinking reaction proceeded as compared with the case in which the coating films were not irradiated with light.

Production of Compound (1)-2

First, as shown below, o-coumaric acid was reacted with a compound (Z) to produce a compound (1)-2.

First, a liquid mixture of o-coumaric acid (1.8 g, 0.010 mol), 1-(3-dimethylaminopropyl)-3-ethylcarbodiimide hydrochloride (2.1 g, 0.012 mol, EDAC HCl) and dried dichloromethane (20 mL) was added, and the liquid mixture was stirred at 0° C. for 1 hour.

Next, the compound (Z) (1.0 g, 0.012 mol) was added to the stirred liquid mixture, and the thus-obtained liquid mixture was stirred for 70 hours to perform the reaction. Finally, it was washed with chloroform.

As a result, the compound (1)-2 was obtained as a light yellow solid (yield 44%).

Regarding the obtained compound (1)-2, the analysis results of ¹H-NMR, ¹³C-NMR, and ESI-MS are shown in Table 4.

Next, it was confirmed that 2-methyl-2-imidazoline (2MI), which is generated by light irradiation to the compound (1)-2, is a stronger base than cyclohexylamine (CyA), which is an aliphatic amine, by a color reaction experiment of phenol red. First, 2MI, CyA and diazabicycloundecene (DBU) were prepared as bases, and 1.5 mL of methanol solution, in which the concentration was prepared at 2.0× 10⁻⁵ mol/L, was added to 1.5 mL of a methanol solution in which each base was dissolved. The basicity of each base was evaluated by measuring the UV-Vis spectrum of each of the solution. The evaluation result is shown in FIG. 17.

Figure 17:
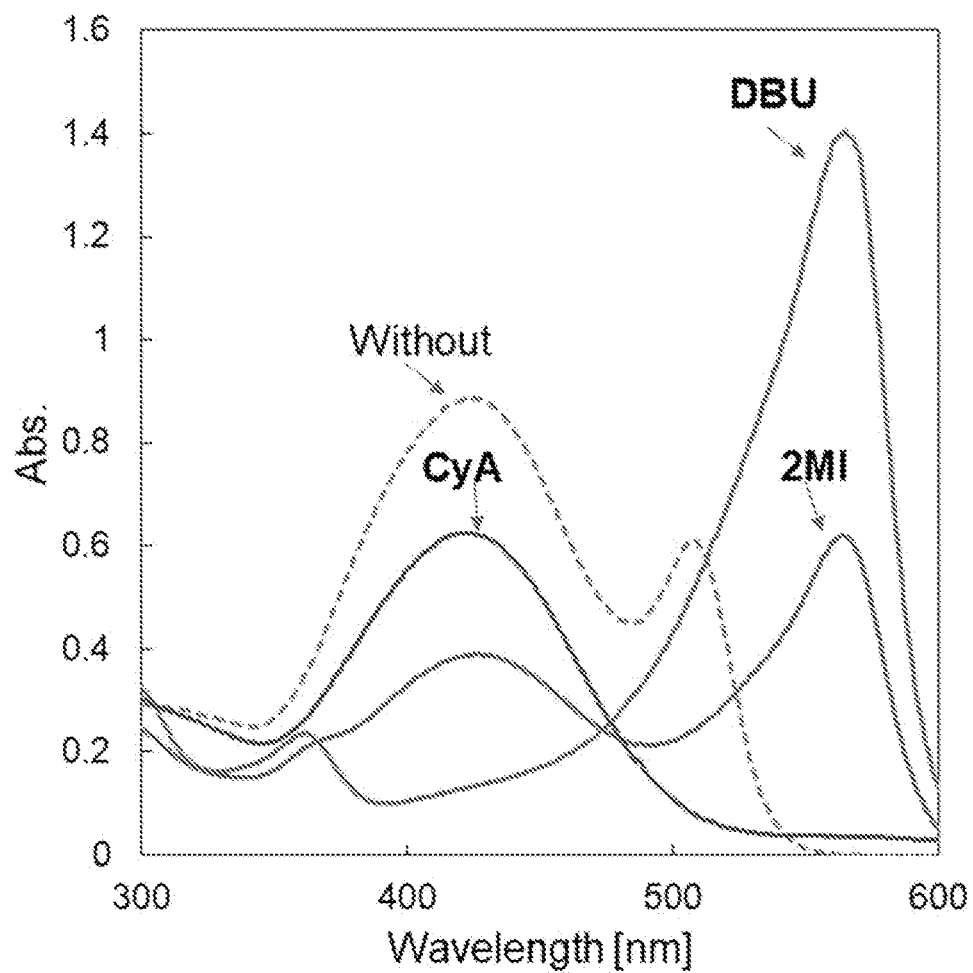
FIG. 17 illustrates the measurement results of the UV-Vis spectra of a methanol solution including 2-methyl-2-imidazoline (2MI), cyclohexylamine (CyA) or diazabicycloundecene (DBU) and phenol red in Example 4.

As shown in FIG. 17, in DBU and 2MI, a peak showing basicity appeared near 570 nm, whereas in CyA, no peak showing basicity appeared near 570 nm. Since the peak intensity near 570 nm depends on the strength of the base, it was found that the basicity of 2MI is weaker than that of DBU, but the basicity of 2MI is stronger than that of CyA.

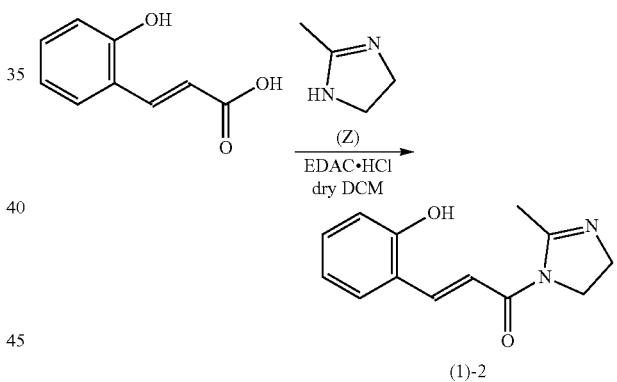

TABLE 4

| ¹H-NMR [δ/ppm] (CDCl₃, 300 MHz) | 2.29 (s, 3H, —CH₃) <br> 3.71 (t, 2H, J = 9.0 Hz, —CONCH₂—) <br> 4.00 (t, 2H, J = 9.0 Hz, —CONCH₂C$\underline{H}$₂—) <br> 6.8-6.9 (m, 2H, Ar—H) <br> 7.00 (d, 1H, J = 18 Hz, —CH=C$\underline{H}$CO—) <br> 7.2-7.7 (m, 2H, Ar—H) <br> 7.87 (d, 1H, J = 18 Hz, —C$\underline{H}$=CHCO—) <br> 10.2 (br, 1H, —OH) |
|---|---|
| ¹³C-NMR [δ/ppm] (d₆-CDCl₃, 75 MHz) | 19, 46, 52 (sp³) 116, 119, 119, <br> 121, 128, 131, 139, 156 (sp²), <br> 157 (C=N), 163 (C=O) |
| ESI-Positive-HR [M + Na]⁺ | Calculated value: 253.09530 <br> Measured value: 253.09440 <br> (Estimated composition formula: C₁₃H₁₄N₂Na₁O₂) <br> Mass difference: −0.09 mmu |

An aqueous solution of the obtained compound (1)-2 was irradiated with light having a wavelength of 365 nm to confirm whether basicity was exhibited by using pH test paper. As a result, the pH test paper was discolored to the basic side.

Production of Compound (4)-3

As shown below, the compound (4)-1 was reacted with a compound (4)-2 to produce a compound (4)-3.

First, a liquid mixture of the compound (4)-1 (2.4 g, 0.010 mol) and dry tetrahydrofuran (20 mL) was added to a liquid mixture of potassium tert-butoxide (1.4 g, 0.012 mol), the compound (4)-2 (5.7 g, 0.012 mol), and dried tetrahydrofuran (20 mL), and the thus-obtained mixture was stirred at 0° C. for 1 hour to react.

Then, the reaction product was purified from the stirred liquid mixture to obtain the compound (4)-3 as a white solid (yield 88%).

Regarding the obtained compound (4)-3, the analysis results of $^1$H-NMR, $^{13}$C-NMR, and ESI-MS are shown in Table 5.

Production of Compound (4)-4

As shown below, a compound (4)-3 was reacted to produce a compound (4)-4.

First, a liquid mixture of compound (4)-3 (2.6 g, 0.080 mol), methanol (20 mL) and 2N sodium hydroxide (20 mL) was stirred for 5 hours to react. After completion of the reaction, the reaction solution was quenched with 5% by mass hydrochloric acid.

Next, dichloromethane was added to the thus-obtained reaction solution, and the reaction solution was washed by shaking in a separating funnel. The washing with dichloromethane was performed three times more, and a total of four times.

As a result, the target compound (4)-4 was obtained as a white solid (yield 84%).

Regarding the obtained compound (4)-4, the analysis results of $^1$H-NMR, $^{13}$C-NMR and ESI-MS are shown in Table 6.

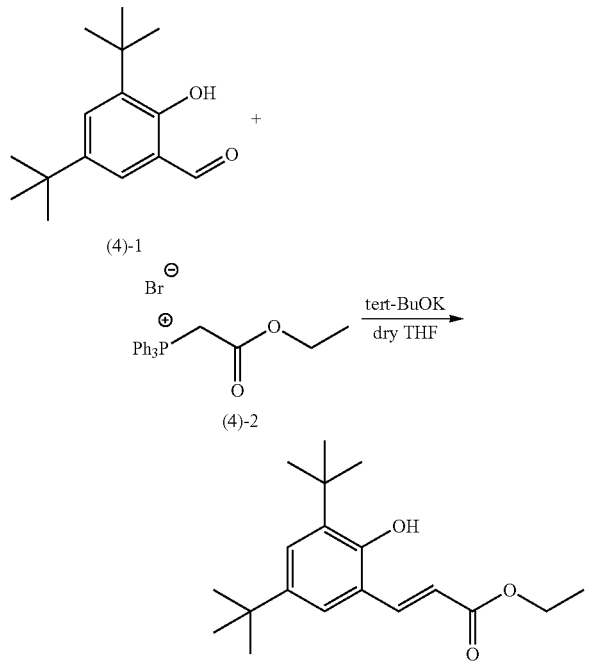

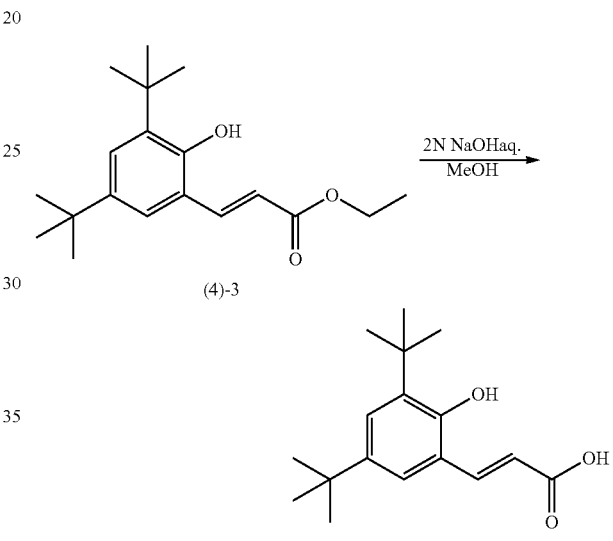

TABLE 5

| $^1$H-NMR [δ/ppm] (CDCl$_3$, 300 MHz) | 1.31 (s, 9H, tert-Bu)<br>1.33 (t, 3H, J = 6.0 Hz, —CH$_2$CH$_3$—)<br>1.44 (s, 9H, tert-Bu)<br>4.27 (q, 2H, J = 6.0 Hz, —CH$_2$CH$_3$—)<br>5.96 (br, 1H, —OH)<br>6.43 (d, 1H, J = 18 Hz, =CHCO—)<br>7.3-7.4 (m, 2H, Ar—H)<br>7.87 (d, 1H, J = 18 Hz, —CH=CHCO—) |
|---|---|
| $^{13}$C-NMR [δ/ppm] (CDCl$_3$, 75 MHz) | 14, 30, 31, 34, 35, 61 (sp$^3$), 119, 122, 122, 126, 137, 141, 143, 151 (sp$^2$), 168 (C=O) |
| ESI-Positive-HR [M + Na]$^+$ | Calculated value: 327.19361<br>Measured value: 327.19373<br>(Estimated composition formula: C$_{19}$H$_{28}$Na$_1$O$_3$)<br>Mass difference: 0.12 mmu |

TABLE 6

| $^1$H-NMR [δ/ppm] (d$_6$-CDCl$_3$, 300 MHz) | 1.27 (s, 9H, tert-Bu)<br>1.37 (s, 9H, tert-Bu)<br>5.96 (d, 1H, J = 16.2 Hz, =CHCOOH)<br>7.3-7.4 (m, 2H, Ar—H)<br>7.87 (d, 1H, J = 16.2 Hz, —CH=CHCO—)<br>8.86 (br, 1H, —OH)<br>12.2 (br, 1H, —COOH) |
|---|---|
| $^{13}$C-NMR [δ/ppm] (d$_6$-CDCl$_3$, 75 MHz) | 30, 32, 34, 35 (sp$^3$), 118, 121, 124, 126, 139, 140, 142, 152 (sp$^2$), 168 (C=O) |
| ESI-Negative-HR [M + H]$^-$ | Calculated value: 275.16472<br>Measured value: 275.16404<br>(Estimated composition formula: C$_{17}$H$_{23}$O$_3$)<br>Mass difference: −0.68 mmu |

Production of Compound (1)-3

As shown below, the compound (4)-4 was reacted with the compound (Z) to produce a compound (1)-3.

First, a liquid mixture of the compound (4)-4 (1.8 g, 0.0067 mol), 1-(3-dimethylaminopropyl)-3-ethylcarbodiimide hydrochloride (1.9 g, 0.010 mol, EDACHCl) and dried dichloromethane (20 mL) was added, and the liquid mixture was stirred at 0° C. for 1 hour.

Next, the compound (Z) (0.84 g, 0.010 mol) was added to the stirred liquid mixture, and the thus-obtained liquid mixture was stirred for 12 hours to perform the reaction. Finally, it was washed with water and acetone.

As a result, the compound (1)-3 was obtained as a light yellow solid (yield 31%).

Regarding the obtained compound (1)-3, the analysis results of $^1$H-NMR, $^{13}$C-NMR, and ESI-MS are shown in Table 7.

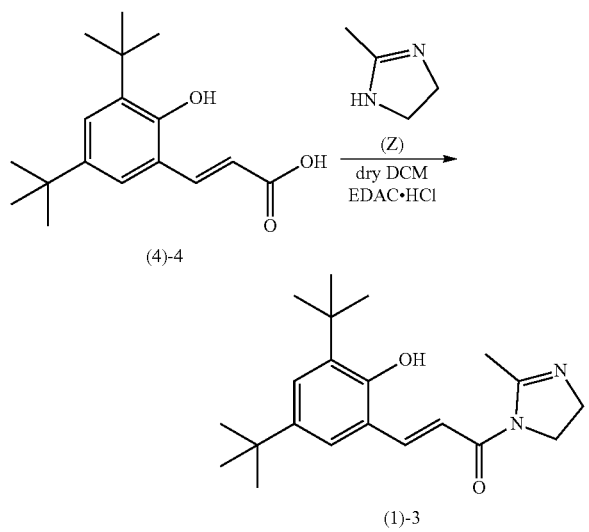

TABLE 7

| $^1$H-NMR [δ/ppm]<br>(d$_6$-CDCl$_3$, 300 MHz) | 1.27 (s, 9H, tert-Bu)<br>1.35 (s, 9H, tert-Bu)<br>2.31 (s, 3H, —CH$_3$)<br>3.70 (t, 2H, J = 9.0 Hz, —CONCH$_2$C$\underline{H}_2$—)<br>4.02 (t, 2H, J = 9.0 Hz, —CONC$\underline{H}_2$CH$_2$—)<br>6.82 (d, 1H, J = 18 Hz, —CH=C$\underline{H}$CO—)<br>7.26 (d, 1H, J = 2.1 Hz, 1H, Ar—$\underline{H}$)<br>7.45 (d, 1H, J = 2.1 Hz, 1H, Ar—H)<br>7.87 (d, 1H, J = 18 Hz, —C$\underline{H}$=CHCO—)<br>8.86 (br, 1H, —OH) |
|---|---|
| $^{13}$C-NMR [δ/ppm]<br>(CDCl$_3$, 75 MHz) | 19, 30, 31, 33, 34, 35, 46, 52 (sp$^3$),<br>118, 122, 123, 127, 138, 142, 143,<br>152 (sp$^2$), 160 (C=N), 164 (C=O) |
| ESI-Positive-HR<br>[M + Na]$^+$ | Calculated value: 365.22050<br>Measured value: 365.22117<br>(Estimated composition formula:<br>C$_{21}$H$_{30}$N$_2$Na$_1$O$_3$)<br>Mass difference: 0.67 mmu |

When the solubility test was performed on the compound (1)-2 and the compound (1)-3, the compound (1)-3 into which the tert-butyl group was introduced, improved in solubility in chloroform, dimethyl sulfoxide and the like as compared with the compound (1)-2.

Test Example 7

(Confirmation of Behavior of Compound (1)-3 in the Solvent under Light Irradiation with a Wavelength of 365 nm)

The above-obtained compound (1)-3 was dissolved in methanol so as to have a concentration of 1.5×10$^{-5}$ mol/L. Then, using an LED lamp, the illuminance was set to 50 mW/cm$^2$, the exposure dose was set to 0, 50, 100, 200 or 350 mJ/cm$^2$, and the obtained methanol solution was irradiated with light having a wavelength of 365 nm. Then, the absorbance of the compound (1)-3 was measured. In Test Example 7, the molar absorption coefficient was $\varepsilon_{365}$=1.2× 10$^4$ L/(mol cm).

In Test Example 7, as compared with the spectrum in the case of the exposure doses of 0 mJ/cm$^2$, that is, the spectrum in the case of no light irradiation, in the spectrum for other doses, both increasing peak and decreasing peak exist, and from this measurement result, it was confirmed that the base was generated from the compound (1)-3 in the reaction shown below by light irradiation.

Test Example 8

(Confirmation of Behavior of Compound (1)-3 in the Solvent under Light Irradiation with a Wavelength of 313 nm)

The above-obtained compound (1)-3 was dissolved in methanol so as to have a concentration of 1.5×10$^{-5}$ mol/L. Then, using a mercury xenon lamp, the illuminance was set to 10 mW/cm$^2$, the exposure dose was set to 0, 50, 100, 200 or 350 mJ/cm$^2$, and the obtained methanol solution was irradiated with light having a wavelength of 313 nm. Then, the absorbance of the compound (1)-3 was measured. In Test Example 8, the molar absorption coefficient was $\varepsilon_{313}$=2.8× 10$^4$ L/(mol cm).

In Test Example 8, as compared with the spectrum in the case of the exposure doses of 0 mJ/cm$^2$, that is, the spectrum in the case of no light irradiation, in the spectrum for other doses, both increasing peak and decreasing peak exist, and from this measurement result, it was confirmed that the base was generated from the compound (1)-3 in the reaction shown below by light irradiation.

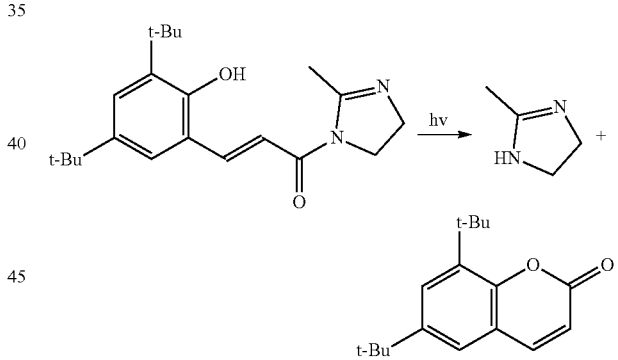

Test Example 9

(Confirmation of Behavior of Compound (1)-3 in Polymer Solid under Light Irradiation)

Polytetramethylene glycol (0.058 g), compound (1)-3 (0.0081 g, 14% by mass with respect to polytetramethylene glycol), and chloroform (0.42 g) were blended and stirred at 25° C. for 1 minute to obtain a resin composition for the test.

Figure 13:
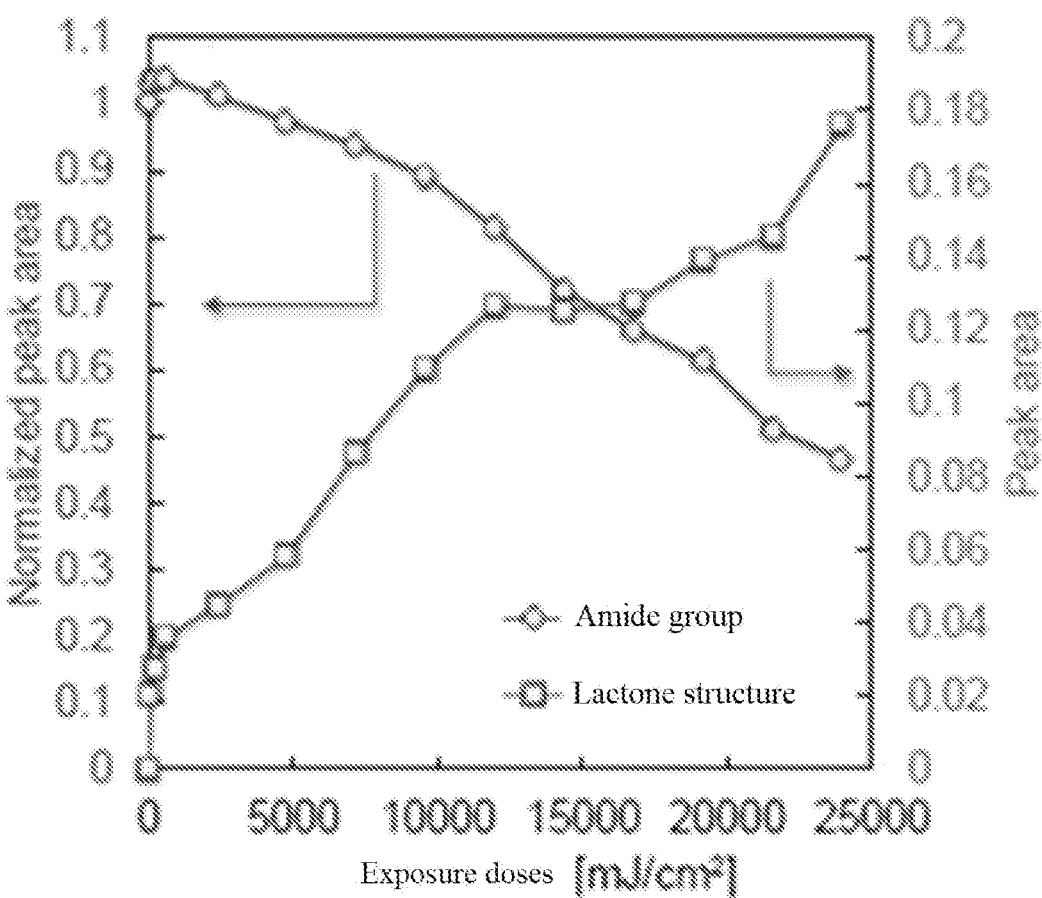
FIG. 13 is a graph illustrating the relationship between the exposure doses in compound (1)-3 and the peak areas of an amide group and a lactone structure in IR spectra in Test Example 9.

Next, the resin composition for the test was applied onto a calcium fluoride plate by a spin coating method under the conditions of 1500 rpm and 20 seconds, the thus obtained coating film was heated for 3 minutes, and then using a mercury xenon lamp, the illuminance was set to 12 mW/cm$^2$, and the coating film was irradiated with light having a wavelength of 313 nm. At this time, at exposure doses of 0 mJ/cm$^2$ to 24000 mJ/cm$^2$, the peak intensity derived from the amide group and the peak intensity derived from the lactone structure were measured with the Fourier transform infrared spectrophotometer (FT-IR). FIG. 13 shows a graph illustrating the relationship between the exposure doses in compound (1)-3 and the peak areas of the amide group and the lactone structure in IR spectrum.

Test Example 10

(Confirmation of Behavior of Compound(1)-3 in the Polymer Solid under Light Irradiation)

Figure 14:
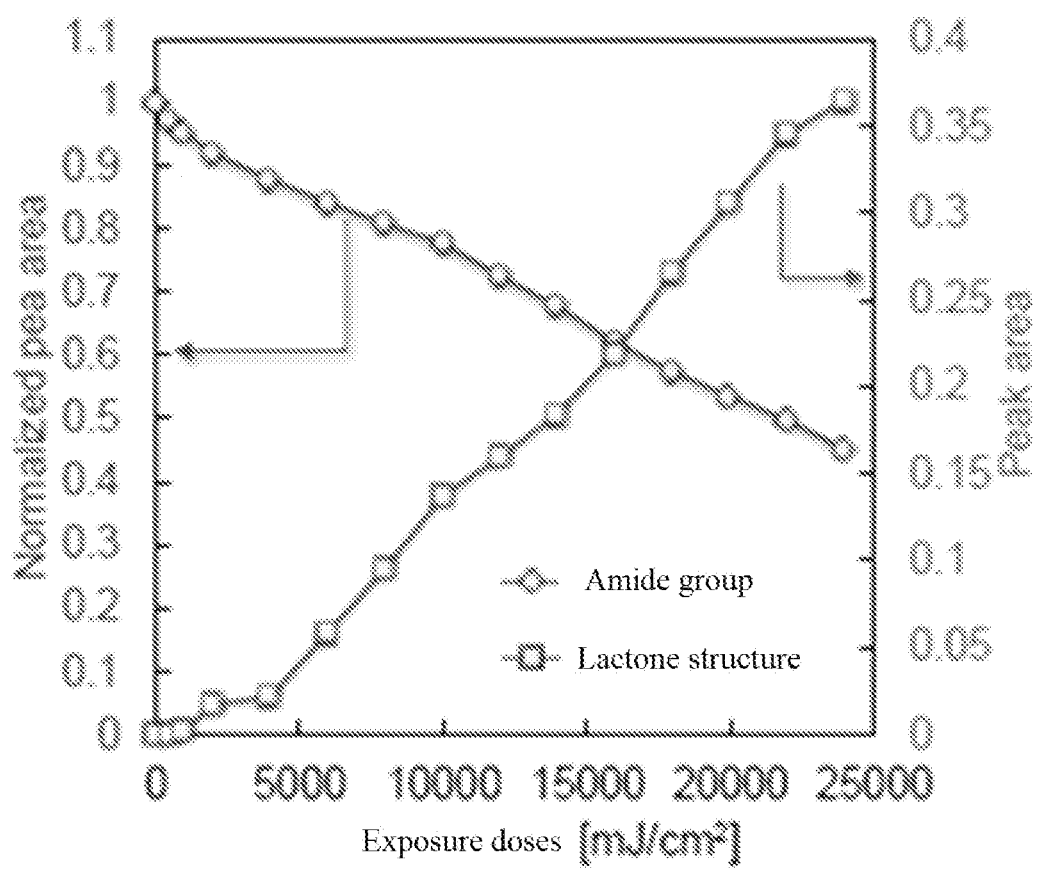
FIG. 14 is a graph illustrating the relationship between the exposure doses in compound (1)-3 and the peak areas of an amide group and a lactone structure in IR spectra in Test Example 10.

In Test Example 9, the same experiment as in Test Example 9 was performed except that an LED lamp was used instead of the mercury xenon lamp, the illuminance was set to 50 mW/cm$^2$, and the coating film was irradiated with light having a wavelength of 365 nm. FIG. 14 shows a graph illustrating the relationship between the exposure doses in compound (1)-3 and the peak areas of the amide group and the lactone structure in IR spectrum.

As is clear from FIGS. 13 and 14, as the exposure doses increased, the peak intensity derived from the amide group decreased and the peak intensity derived from the lactone structure increased. This is because the same reaction as in Test Example 7 and Test Example 8 was generated by light irradiation.

Example 5

(Production of Photoreactive Composition)

Trimethylolpropane triacrylate (0.14 g), the aforementioned base-reactive compound (9)-401 (0.28 g, a ratio of the mercapto group with respect to the acryloyl group in trimethylolpropane triacrylate: 100 mol %), the compound (1)-3 (0.013 g, 10 mol % with respect to trimethylolpropane triacrylate), and chloroform (0.43 g) were blended and stirred at 25° C. for 1 minute to obtain a photoreactive composition.

(Production of Reaction Product)

The photoreactive composition obtained above was applied onto a calcium fluoride plate by a spin coating method under the conditions of 1000 rpm and 10 seconds. Next, this coating film (photoreactive composition layer) was heated (prebaked) at 60° C. for 1 minute, and then using an LED lamp, the illuminance was set to 50 mW/cm$^2$, and the coating film was irradiated with light having a wavelength of 365 nm. Exposure doses were adjusted to 1000 mJ/cm$^2$. From the above, it was attempted that a thiorate anion was generated from the compound (9)-401 by the action of the base generated, by light irradiation, from the compound (1)-3, and that a reaction product was produced by a cross-linking reaction of the generated thiorate anion and trimethylolpropane triacrylate.

Example 6

It was attempted to produce a reaction product in the same manner as in Example 5 except that a mercury xenon lamp was used instead of the LED lamp, the illuminance was set to 10 mW/cm$^2$, and the coating film was irradiated with light of 313 nm.

In Example 5 and Example 6, the peak intensity was measured with the Fourier transform infrared spectrophotometer (FT-IR), and the change in the peak area of the acryloyl group by light irradiation and the change in the peak area of the mercapto group by light irradiation were evaluated. As a result, it was confirmed that the acryloyl group and the mercapto group were consumed by the light irradiation of the coating films and the cross-linking reaction was proceeding. The results are shown in FIG. 15 and FIG. 16.

Figure 15:
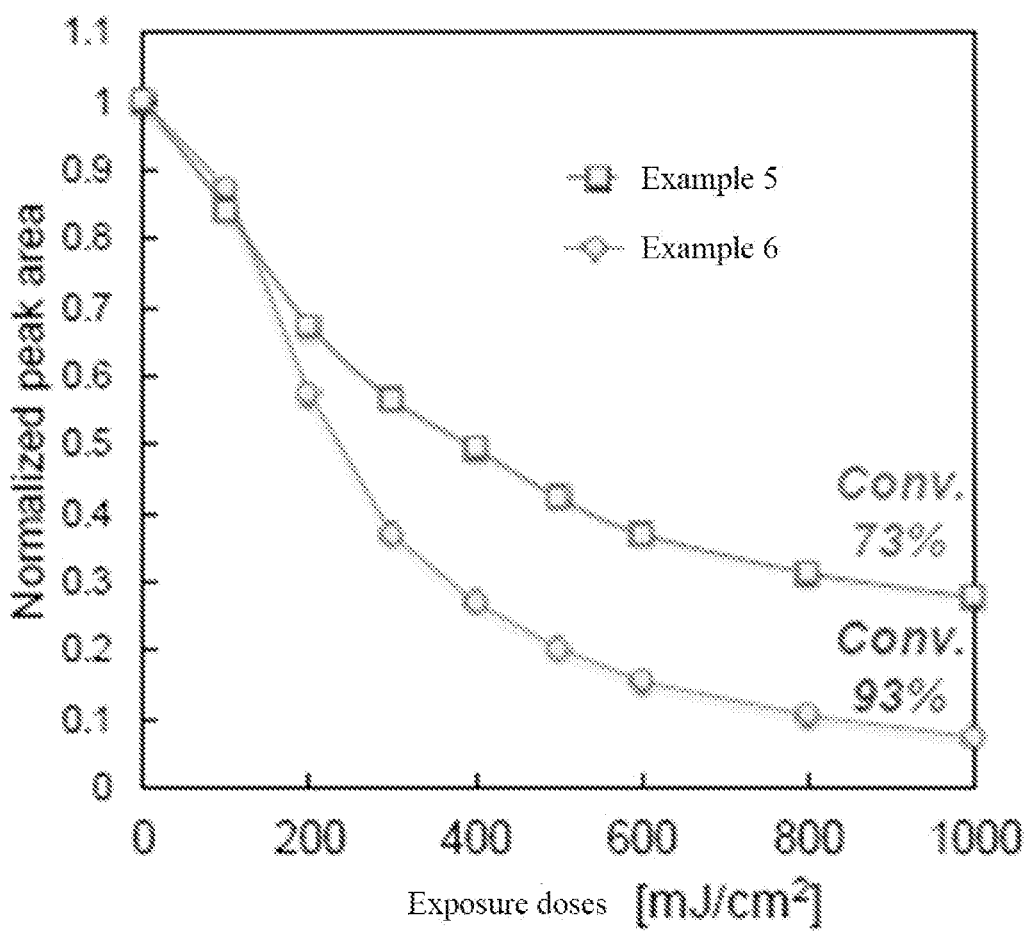
FIG. 15 is a graph illustrating the relationship between the heating time and the peak areas derived from an acryloyl group under the light irradiation condition in Example 5 and Example 6.
Figure 16:
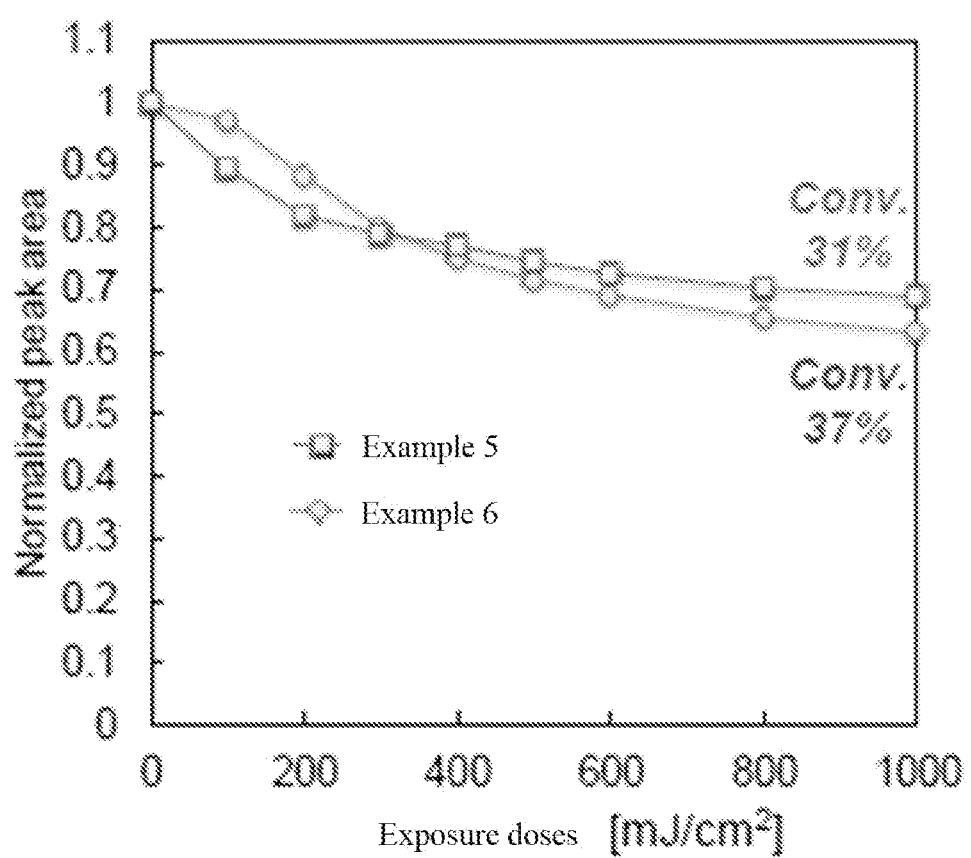
FIG. 16 is a graph illustrating the relationship between the heating time and the peak areas derived from a mercapto group under the light irradiation condition in Example 5 and Example 6.

As shown in FIG. 15 and FIG. 16, it was found that the acryloyl group and the mercapto group were consumed by the light irradiation of the coating films and the cross-linking reaction was proceeding. Further, it was found that in Example 6 in which the coating film was irradiated with light of 313 nm, the crosslinking reaction was more advanced than in Example 5 in which the coating film was irradiated with light of 365 nm. The reason why the results different from those of Examples 2 and 3 were obtained is considered that in compound (1)-3, the absorption spectrum was lengthened due to the introduction of the tert-butyl group and the cross-linking reaction proceeded more when the coating film was irradiated with light of 313 nm, unlike the case in which the compound (1)-1 was used.

The disclosure of Japanese Patent Application No. 2019-164946 filed on Sep. 10, 2019 is herein incorporated by reference in its entity.

All documents, patent applications, and technical standards described herein are herein incorporated by reference, as if each individual document, patent application, and technical standard were specifically and individually indicated to be incorporated by reference.

The invention claimed is:

1. A photobase generator, comprising a compound including a first skeleton represented by the following formula (a), and a second skeleton including a nitrogen atom bonding to a bonding position of the first skeleton to form an amide group, wherein the compound generates a base, in which a hydrogen atom is bonding with the nitrogen atom of the second skeleton, by light irradiation, and a pKa of a conjugate acid of the base in water is 12 or more:

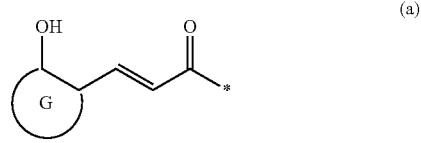

wherein, in formula (a), G is a divalent aromatic group, and * represents the bonding position with the nitrogen atom.

2. The photobase generator according to claim 1, wherein the second skeleton is a structure represented by the following formula (1)-12, (1)-13, or (1)-14:

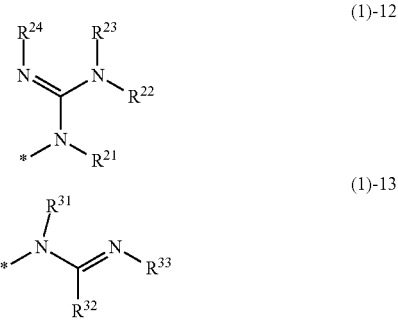

-continued

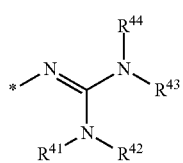
(1)-14 wherein, in formula (1)-12 to formula (1)-14, each of $R^{22}$, $R^{23}$, $R^{24}$, $R^{32}$, $R^{33}$, $R^{41}$, $R^{42}$, $R^{43}$, and $R^{44}$ independently represents a hydrogen atom or a hydrocarbon group that may have a substituent; each of $R^{21}$ and $R^{31}$ independently represents a hydrocarbon group that may have a substituent; * represents a bonding position that forms a single bond by combining with * in formula (a); two or more of $R^{21}$ to $R^{24}$ are optionally bonding to each other to form a ring structure; two or more of $R^{31}$ to $R^{33}$ are optionally bonding to each other to form a ring structure; and two or more of $R^{41}$ to $R^{44}$ are optionally bonding to each other to form a ring structure.

3. A photobase generator, comprising a compound including a first skeleton represented by the following formula (a), and a second skeleton that includes a nitrogen atom bonding to a bonding position of the first skeleton to form an amide group and that is represented by the following formula (1)-12, (1)-13, or (1)-14,
wherein the compound generates a base, in which a hydrogen atom is bonding with the nitrogen atom of the second skeleton, by light irradiation:

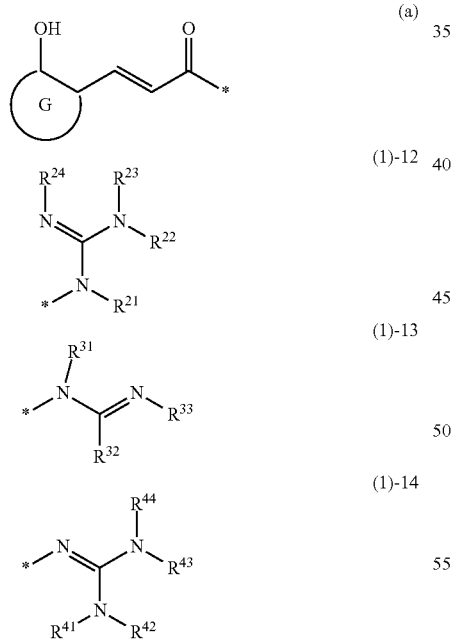

wherein, in formula (a), G is a divalent aromatic group, and * represents the bonding position with the nitrogen atom; and in formula (1)-12 to formula (1)-14, each of $R^{22}$, $R^{23}$, $R^{24}$, $R^{32}$, $R^{33}$, $R^{41}$, $R^{42}$, $R^{43}$, and $R^{44}$ independently represents a hydrogen atom or a hydrocarbon group that may have a substituent; each of $R^{21}$ and $R^{31}$ independently represents a hydrocarbon group that may have a substituent; * represents a bonding position that forms a single bond by combining with * in formula (a); two or more of $R^{21}$ to $R^{24}$ are optionally bonding to each other to form a ring structure; two or more of $R^{31}$ to $R^{33}$ are optionally bonding to each other to form a ring structure; two or more of $R^{41}$ to $R^{44}$ are optionally bonding to each other to form a ring structure; and in a case in which a structure represented by in formula (1)-13 has a ring structure formed by bonding $R^{31}$ and $R^{33}$ to each other, the ring structure does not exhibit aromaticity.

4. A compound, comprising a first skeleton represented by the following formula (a), and a second skeleton including a nitrogen atom bonding to a bonding position of the first skeleton to form an amide group,
wherein the compound generates a base, in which a hydrogen atom is bonding with the nitrogen atom of the second skeleton, by light irradiation, and a pKa of a conjugate acid of the base in water is 12 or more, and the second skeleton is a structure represented by the following formula (1)-12, or (1)-13:

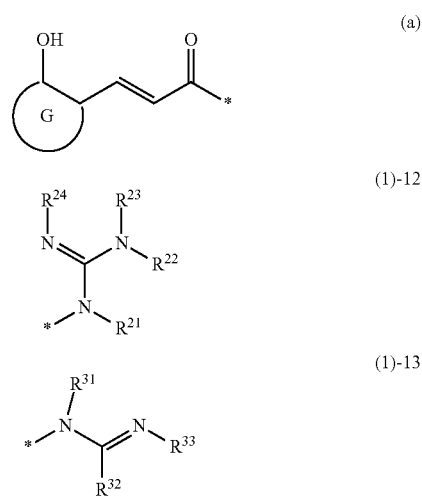

wherein, in formula (a), G is a divalent aromatic group; and * represents the bonding position with the nitrogen atom; in formula (1)-12 and formula (1)-13, each of $R^{22}$, $R^{23}$, $R^{24}$, $R^{32}$, and $R^{33}$ independently represents a hydrogen atom or a hydrocarbon group that may have a substituent; each of $R^{21}$ and $R^{31}$ independently represents a hydrocarbon group that may have a substituent; * represents a bonding position that forms a single bond by combining with * in the formula (a); two or more of $R^{21}$ to $R^{24}$ are optionally bonding to each other to form a ring structure; and two or more of $R^{31}$ to $R^{33}$ re optionally bonding to each other to form a ring structure.

5. A compound, comprising a first skeleton represented by the following formula (a), and a second skeleton that includes a nitrogen atom bonding to a bonding position of the first skeleton to form an amide group and that is represented by the following formula (1)-12, or (1)-13,
wherein the compound generates a base, in which a hydrogen atom is bonding with the nitrogen atom of the second skeleton, by light irradiation:

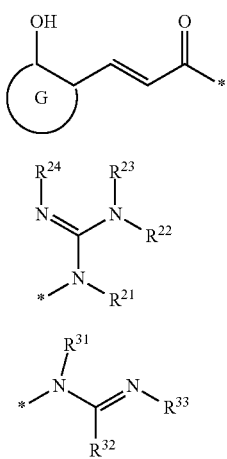

wherein, in formula (a), G is a divalent aromatic group, and * represents the bonding position with the nitrogen atom; and in formula (1)-12 and formula (1) 13, each of $R^{22}$, $R^{23}$, $R^{24}$, $R^{32}$, and $R^{33}$ independently represents a hydrogen atom or a hydrocarbon group that may have a substituent; each of $R^{21}$ and $R^{31}$ independently represents a hydrocarbon group that may have a substituent; * represents a bonding position that forms a single bond by combining with * in the formula (a); two or more of $R^{21}$ to $R^{24}$ are optionally bonding to each other to form a ring structure; two or more of $R^{31}$ to $R^{33}$ are optionally bonding to each other to form a ring structure; and in a case in which a structure represented by in formula (1)-13 has a ring structure formed by bonding $R^{31}$ and $R^{33}$ to each other, the ring structure does not exhibit aromaticity.

6. A photoreactive composition, comprising:
the photobase generator according to claim 1; and
a base-reactive compound,
wherein the base-reactive compound includes a functional group that is converted, by the action of a base, into a group exhibiting reactivity, or includes a group that reacts in response to the action of a base.

7. A reaction product obtained by reacting the photoreactive composition according to claim 6.

8. A photoreactive composition, comprising:
the photobase generator according to claim 2; and
a base-reactive compound,
wherein the base-reactive compound includes a functional group that is converted, by the action of a base, into a group exhibiting reactivity, or includes a group that reacts in response to the action of a base.

9. A photoreactive composition, comprising:
the photobase generator according to claim 3; and
a base-reactive compound,
wherein the base-reactive compound includes a functional group that is converted, by the action of a base, into a group exhibiting reactivity, or includes a group that reacts in response to the action of a base.

* * * * *